United States Patent [19]
Jacobs et al.

[11] Patent Number: 5,976,837
[45] Date of Patent: *Nov. 2, 1999

[54] SECRETED PROTEINS AND POLYNUCLEOTIDES ENCODING THEM

[75] Inventors: Kenneth Jacobs, Newton; John M. McCoy, Reading; Edward R. LaVallie, Harvard; Lisa A. Racie; David Merberg, both of Acton; Maurice Treacy, Chestnut Hill; Vikki Spaulding, Billerica; Michael J. Agostino, Andover, all of Mass.

[73] Assignee: Genetics Institute, Inc., Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/960,022

[22] Filed: Oct. 29, 1997

Related U.S. Application Data

[63] Continuation-in-part of application No. 08/815,047, Mar. 14, 1997, abandoned.

[51] Int. Cl.$^6$ ..................................................... C12N 15/00
[52] U.S. Cl. ................... 435/69.1; 435/91.4; 435/252.3; 435/320.1; 536/23.1; 536/23.5; 536/24.1; 536/24.31; 530/350
[58] Field of Search .................................. 435/69.1, 91.4, 435/252.3, 320.1; 536/23.1, 23.5, 24.1, 24.31; 530/350

[56] References Cited

U.S. PATENT DOCUMENTS

| | | | |
|---|---|---|---|
| 5,536,637 | 7/1996 | Jacobs | 435/6 |
| 5,650,313 | 7/1997 | Adams | 435/193 |

FOREIGN PATENT DOCUMENTS

| | | |
|---|---|---|
| 0510691 | 10/1992 | European Pat. Off. . |
| 796913A2 | 9/1997 | European Pat. Off. . |
| 08154684 | 6/1996 | Japan . |
| WO90/05780 | 5/1990 | WIPO . |
| WO90/14432 | 11/1990 | WIPO . |
| WO94/07916 | 4/1994 | WIPO . |
| WO95/14772A1 | 6/1995 | WIPO . |
| WO95/18974 | 7/1995 | WIPO . |
| WO96/17925 | 6/1996 | WIPO . |
| WO96/23410A1 | 8/1996 | WIPO . |
| WO97/07198 | 2/1997 | WIPO . |
| WO97/25427 | 7/1997 | WIPO . |
| WO98/01566A1 | 1/1998 | WIPO . |

OTHER PUBLICATIONS

Suzuki et al. (1985) An Introduction to Genetic Analysis, Third Edition. WH Freeman and Co., NY, New York.
Hillier et al. (1995) EST database, Accession No. R60369.
Aufray et al. (1995) EST database, Accession No. F05256.
Hillier et al. (Jan. 4, 1996) EST Database, Accession No. N29202.
C. Aufray et al., "The Genexpress cDNA program" EMBL Sequence Database, Feb. 12, 1995, Heidelberg, FRG, H. sapiens partial cDNA sequence; clone c–05b05; Accession No. F05256.
L. Hillier et al., "The WashU–Merck EST Project" EMBL Sequence Database, May 29, 1995, Heidelberg, FRG, yh04b03.r1 Homo sapiens cDNA clone 42053 5'; Accession No. R60369.
L. Hillier et al., "The WashU–Merck EST Project" EMBL Sequence Database, May 17, 1996, Heidelberg, FRG, zc18g02.r1 SOares parathyroid tumor NbHPA Homo sapiens cDNA clone 322706 5'; Accession No. W39550.

(List continued on next page.)

*Primary Examiner*—Robert A. Wax
*Assistant Examiner*—Enrique D. Longton
*Attorney, Agent, or Firm*—Suzanne A. Sprunger; Scott A. Brown

[57] ABSTRACT

Novel polynucleotides and the proteins encoded thereby are disclosed.

14 Claims, 2 Drawing Sheets

OTHER PUBLICATIONS

Adams, M. D. et al. (1993) "3,400 new expressed sequence tags identify diversity of transcripts in human brain" *Nature Genetics* 4(3):256–267.

Jacobs, K. et al. (1995) "A novel method for isolating eukaryotic cDNA clones encoding secreted proteins" *J Cell Biochem* 21A:19.

Kaufman, R. J., et al. (1989) "Effect of von Willebrand factor coexpression on the synthesis and secretion of factor VIII in chinese hamster ovary cells" *Mol Cell Biol* 9(3):1233–1242.

Kaufman, R. J. et al. (1989) "The phosphorylation state of eukaryotic initiation factor 2 alters translation effeciency of specific mRNAs" *Mol Cell Biol* 9(3):946–958.

Kaufman, R. J. et al. (1991) "Improved vectors for stable expression of foreign genes in mammalian cells by use of the untranslated leader sequence from EMC virus" *Nucleic Acids Res* 19(16):4485–4490.

GenBank Accession No. AA018129; Jan. 30, 1997.
GenBank Accession No. AA018130; Jan. 30, 1997.
GenBank Accession No. AA044667; May 11, 1997.
GenBank Accession No. AA074479; Oct. 7, 1996.
GenBank Accession No. AA074480; Oct. 7, 1996.
GenBank Accession No. AA091907; Oct. 24, 1996.
GenBank Accession No. AA094806; Oct. 25, 1996.
GenBank Accession No. AA152125; May 19, 1997.
GenBank Accession No. AA156816; Dec. 11, 1996.
GenBank Accession No. AA156896; Dec. 11, 1996.
GenBank Accession No. AA165612; Dec. 18, 1996.
GenBank Accession No. AA165621; Dec. 18, 1996.
GenBank Accession No. AA166738; Dec. 19, 1996.
GenBank Accession No. AA167018; Dec. 19, 1996.
GenBank Accession No. AA211896; Aug. 13, 1997.
GenBank Accession No. AA236003; Aug. 13, 1997.
GenBank Accession No. AA258818; Aug. 13, 1997.
GenBank Accession No. AA258932; Aug. 13, 1997.
GenBank Accession No. AA261860; Aug. 13, 1997.
GenBank Accession No. AA331682; Apr. 21, 1997.
GenBank Accession No. AA341059; Apr. 21, 1997.
GenBank Accession No. AA345758; Apr. 21, 1997.
GenBank Accession No. AA371039; Apr. 21, 1997.
GenBank Accession No. AA435533; Nov. 9, 1997.
GenBank Accession No. AA478628; Aug. 8, 1997.
GenBank Accession No. AA480905; Aug. 14, 1997.
GenBank Accession No. AA488853; Aug. 15, 1997.
GenBank Accession No. AA488873; Aug. 15, 1997.
GenBank Accession No. AA488925; Aug. 15, 1997.
GenBank Accession No. AA490590; Aug. 15, 1997.
GenBank Accession No. AA490739; Aug. 15, 1997.
GenBank Accession No. AA490749; Aug. 15, 1997.
GenBank Accession No. AA490784; Aug. 15, 1997.
GenBank Accession No. AA491229; Aug. 18, 1997.
GenBank Accession No. AA491236; Aug. 18, 1997.
GenBank Accession No. AA521187; Aug. 20, 1997.
GenBank Accession No. AA553859; Sep. 8, 1997.
GenBank Accession No. AA574142; Sep. 12, 1997.
GenBank Accession No. C01426; Jul. 11, 1996.
GenBank Accession No. C18400; Sep. 9, 1996.
GenBank Accession No. D79301; Dec. 14, 1995.
GenBank Accession No. D82419; Aug. 9, 1996.
GenBank Accession No. H22250; Jul. 6, 1995.
GenBank Accession No. H42546; Jul. 31, 1995.
GenBank Accession No. H42547; Jul. 31, 1995.
GenBank Accession No. H43433; Jul. 31, 1995.
GenBank Accession No. H43996; Jul. 31, 1995.
GenBank Accession No. H43997; Jul. 31, 1995.
GenBank Accession No. H84090; Nov. 13, 1995.
GenBank Accession No. H84091; Nov. 13, 1995.
GenBank Accession No. N20622; Dec. 18, 1995.
GenBank Accession No. N29202; Jan. 4, 1996.
GenBank Accession No. N34063; Jan. 11, 1996.
GenBank Accession No. N34090; Jan. 11, 1996.
GenBank Accession No. N34097; Jan. 11, 1996.
GenBank Accession No. N57554; Feb. 22, 1996.
GenBank Accession No. N64079; Mar. 1, 1996.
GenBank Accession No. N87578; Apr. 1, 1996.
GenBank Accession No. N92776; Apr. 5, 1996.
GenBank Accession No. R01227; Mar. 31, 1995.
GenBank Accession No. R01340; Mar. 31, 1995.
GenBank Accession No. R34375; May 2, 1995.
GenBank Accession No. R47909; May 18, 1995.
GenBank Accession No. R48013; May 18, 1995.
GenBank Accession No. R77825; Jun. 7, 1995.
GenBank Accession No. R78198; Jun. 7, 1995.
GeneSeq Accession No. R79648; Dec. 6, 1995.
GeneSeq Accession No. R79649; Dec. 6, 1995.
GeneSeq Accession No. R79650; Dec. 6, 1995.
GenBank Accession No. R80959; Jun. 9, 1995.
GenBank Accession No. R80972; Jun 9, 1995.
GenBank Accession No. R81082; Jun. 9, 1995.
GeneSeq Accession No. R99264; Nov. 7, 1996.
GeneSeq Accession No. T20014; Jul. 17, 1996.
GenBank Accession No. U23517; Dec. 30, 1997.
GeneSeq Accession No. W05315; Apr. 3, 1997.
GenBank Accession No. W19267; Oct. 10, 1996.
GenBank Accession No. W19342; May 3, 1996.
GenBank Accession No. W19430; May 3, 1996.
GeneSeq Accession No. W25113; Nov. 12, 1997.
GenBank Accession No. W25524; May 7, 1996.
GeneSeq Accession No. W37496; Apr. 20, 1998.
GeneSeq Accession No. W44375; Jun. 10, 1998.
GenBank Accession No. W79656; Oct. 17, 1996.
GenBank Accession No. W81357; Oct. 17, 1996.
GenBank Accession No. Z39797; Sep. 21, 1995.
C. Auffray et al., "The Genexpress cDNA program" EMBL Sequence Database, Sep. 21, 1995, Heidelberg, FRG, H. Sapiens partial cDNA sequence; clone c–1we02; Accession No. Z44263.

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 1117 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
GTTACCTCTC TGTAGCTATG TTTTCCCATG GTTGTTTTAA GAGGAATAGA AGAAAGGAAA      60

ACAGCTTGTG AAAATCCTAA GTTGTATTTG AACGAGCAAG CTGTGTTTCC TCATTAAAAC     120

ATTTATTTCG CATTTGATGG TCCATAACTG CCCATTTACC TCAGGATGCC TCCATATGAT     180

GAAAATAAGA ACAGAGTTGA AAGAAGTCTC CATAAACACA ACGCACATTG GCAAATGTCA     240
```

```
TATTCTTGTT CCTTAAGGGA TTAGAGAACA CTTTCTTCTC TTTGTCTTTG CCCCCAAAGT      300

AAAAGCTATA AGCTTTTATA ATTAAATAAT AAGACTGAAT AACCATAAGC GCAAATAATA      360

TGTAGTATTA TGAGAAATAC TGGGAAAAAG GACACTTACT GTGTGACTTA AATTGATTAA      420

AGGGTTATTC AGTTCAACTC TCTTGAATCT AATTAGTATT TTTGTGTCAT TTATTATTAT      480

AGGGCACACA TTTTTTACAT TTGATTTAAC TTGACCAAAA TTAAATGAGC AAATGTTTAT      540

TGCTATGTCC ATTGTTTTCC TTTCTCTGTC ACTGTTAAAA AGAGGAGCCA TGGCTTCTGC      600

TTCTTCTGTG TATTCTCCAT TAGACCTTCT TCATCCACCC TCTTCCCCAT CCCTTTCAGC      660

TCTGAAGGGT CTATAAATGA AAGTGGGTAC CAACTGATTC AATAGGACTT ATATCTTACC      720

AAATAACGTT TTATTGTCTT TGTTCTATGT ATTTGCAGAG AAATTGTAAG TATCTTTAAA      780

ACCAATTAAC AAAGCCCTGT GGGTCTTTCA ATCAAGACCT TTGTAAACAT CTCTACTAGC      840

CCATACTCCC CCAAACTTCT TGCACATGGT AGAAGATGAC ATTAAATAAA GCACATTATA      900

AGGTGCAATG AGCTTTATTC TAAAAATATT GTCTGGATGT GAAAGTAAGT TCTTGTTCAT      960

AAAATGTTAT TAGTAAAATG TTATTAGATT AAAATTATGG AGTAAGCATT TGGCAAACTG     1020

ATTGACTCTT CACTGGAAAG ACCAGGCTTT TTAGGACACA TTTCTGTTCA TGCTTAAGGT     1080

CAGAAGTCAA TCAAAGGCAA CCAAAAAAAA AAAAAAA                              1117

(2) INFORMATION FOR SEQ ID NO:2:

(i) SEQUENCE CHARACTERISTICS:
        (A) LENGTH: 47 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Met Phe Ile Ala Met Ser Ile Val Phe Leu Ser Leu Ser Leu Leu Lys
1               5                   10                  15

Arg Gly Ala Met Ala Ser Ala Ser Ser Val Tyr Ser Pro Leu Asp Leu
            20                  25                  30

Leu His Pro Pro Ser Ser Pro Ser Leu Ser Ala Leu Lys Gly Leu
        35                  40                  45

(2) INFORMATION FOR SEQ ID NO:3:

(i) SEQUENCE CHARACTERISTICS:
        (A) LENGTH: 4078 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

GTGGAGAGGA GGTGGCAGCG GCCCGGGAGG CCGGAGCCAA GCCAGCGACC CACCATGGAG       60

ACCCGCTACA AACCTGAAGAG TCCGGCTGTT AAACGTTTAA TGAAAGAAGC GGCAGAATTG     120

AAAGATCCAA CAGATCATTA CCATGCGCAG CCTTTAGAGG ATAACCTTTT TGAATGGCAC      180

TTCACGGTTA GAGGGCCCCC AGACTCCGAT TTTGATGGAG GAGTTTATCA CGGGCGGATA      240

GTACTGCCAC CAGAGTATCC CATGAAACCA CCAAGCATTA TTCTCCTAAC GGCTAATGGT      300

CGATTTGAAG TGGGCAAGAA AATCTGTTTG AGCATCTCAG GCCATCATCC TGAAACTTGG      360

CAGCCTTCGT GGAGTATAAG GACAGCATTA TTAGCCATCA TTGGGTTTAT GCCAACAAAA      420

GGAGAGGGAG CCATAGGTTC TCTAGATAAC ACTCCTGAGG AAAGAAGAGC ACTTGCCAAA      480
```

```
AAATCACAAG ATTTCTGTTG TGAAGGATGT GGCTCTGCCA TGAAGGATGT CCTGTTGCCT      540

TTAAAATCTG GAAGCGATTC AAGCCAAGCT GACCAAGAAG CCAAAGAACT GGCTAGGCAA      600

ATAAGCTTTA AGGCAGAAGT CAATTCATCT GGAAACACTA TCTCTGAGTC AGACTTAAAC      660

CACTCTTTTT CACTAACTGA TTTACAAGAT GATATACCTA CAACATTCCA GGGTGCTACG      720

GCCAGTACAT CGTACGGACT CCAGAATTCC TCAGCAGCAT CCTTTCATCA ACCTACCCAA      780

CCTGTAGCTA AGAATACCTC CATGAGCCCT CGACAGCGCC GGGCCCAGCA GCAGAGTCAG      840

AGAAGGTTGT CTACTTCACC AGATGTAATC CAGGGCCACC AGCCAAGAGA CAACCACACT      900

GATCATGGTG GGTCAGCTGT ACTGATTGTC ATCCTGACTT TGGCATTGGC AGCTCTTATA      960

TTCCGACGAA TATATCTGGC AAACGAATAC ATATTTGACT TGAGTTATA ATATGGTTTT      1020

GTGACTTATG AGCTGTGACT CAACTGCTTC ATTAAACATT CTGCATTGGG TATAATCTAA     1080

GAATTGTTTA CAAAAGATT ATTTTGTATT TACCCTTCAT TCCTTTTTTT GATCCTTGTA      1140

AGTTTAGTAT AAATATATCT AGACATTCAG ACTGTGTCTA GCAGTTACGT CCTGCTTAAA     1200

GGGACTAGAA GTCAAAGTTC CTTGTCTCAC TATTTGATCT GCTTTGCAGG GAAATAACTT     1260

GTTTTTTCTC ATGTTTCATC TTCTTTTTAT GTAAATTTGT AATACTTTCC TATATTGCCC     1320

TTTGAAATTT TTGGATAAAA GATGATGTTT TAAGTTCCAA TGAGTATTAC TAGTTACTCA     1380

ATACCACTTA TTGAGTACTC TGTTTCTACG TATGTAGAAT GTATAGGGAT AGAAGAGTTG     1440

AAAAGGGAAA GCAAAACTCC TCAAGTAGCT TCCTTAAAAT GTCATTCATA GGAGATGTAC     1500

TGGAATTGCT CATTCTGTGA CTTTATTTGT GTCCTAAACA TTCTTCAGTG AAAATAATTT     1560

TATTTCAGTC AAACATTTAT GAGGAAATGA GATCACATCT TTGTCACTGG ATGCTACTTG     1620

AAGAGGGAGT ACTTTGTAAC CACTTTGATA TGCTGTTATC ACCACCCCCT GCCCTCTGCT     1680

GCCATAATCA CACAAATTTA AAAGAAAGA AAACAGTCTT CCATAGATTT TTAAGGAAGA      1740

AAGGGCCCAA GCCAGGAGAT CGCTTGGTTT TCTTCCAGAA GTTAAATGGG GGGATCTGAA     1800

GATTTGAATG TTTGGTCTGC TTTGAAATGT ATGTCTTTTG GGATGTATTA TATGCCTAGC     1860

TTTATAATCA GTATAAATTT TAATTATTCC AGGAATATGC ATAATATTGA AATATTTCAT     1920

GTCCTATTTT AATAGAAAAC CTCAGGGCCC AAGTAACAGT GATAGAAGTT AGAAAAACCT     1980

TTACTTAGAA TTGTCCACCT AGTCAGAGCC CAAGAAAGAA TTTTCAGTGG AAAAATCAAT     2040

ATATAACTTA GTGCTAGCTA GCGCCACAGA CTCTAGTAGA TAATATTATC ATCATAATGG     2100

CTGGTGAAAC CATATAATCA CAGAAAAACA TTGCCTTCAG CATGTTCAGT TCGCAGCACT     2160

GAGGGCACTC TTGAGGGTGT TGTTAATGAA GATTTAATTT TTAAATACAG GTGGTTCCAA     2220

GCTTTCAAAT AGGTTATGCT CCAAAAGTGT TATTTGTAAG TTAATTTTTT TACAAGTCAA     2280

ACAATGTTGG AAGTGGTATT TAGGTTCTAG ATCGGTCCAC GAAAGTTAGC CCATATGTAT     2340

ATCTTGAATA GTATAGGGGA GGGTATTCAT AAAGTCCTTA TGTGGTTTTA ACTAAGTGAA     2400

ATTATGGACA AGAGAAATAA TTGTAAAATC GTCTTAAAGG AAAATTTAAT TTTTACTCCT     2460

GTTTATGGGA CATTCGTTCT ATTAACTGTC AGACACAATT TCTGTTTTCA TCTGAGAGCC     2520

AGTTTTCCTT TATTTCTACA TCTAAAATAA GAACATATTG TACATTATTA TATAATACAG     2580

AATTGTCTTA AACTTTAATA AATTCGCATT TTAAAGGTGT TTACAGATTA TTTTTTATAT     2640

CTGTAGCTGA ATTTGTTAAA GTCTAAAAAG CTCAAGGACT TTATGAAGAT CTCATTATAT     2700

GAGGAAAATC ATAGGTTACC ATTTTATAAC TCTATTGCCA TAAGAAAATA CACTCTAAAA     2760

TCTTGATTTG AAACATATTA GAAACCTTGA TTCAGTGCTC AGTGGTCTCC TAGTAAGAAG     2820

TCACCGACGG TAGCGTCATA TGAGAAGAAA GAAATCCCCA CCACCTCAAC CTCTGCTGAG     2880
```

-continued

```
ATTGTGTGCT AGGAACAGCC TTCCCTCCGT TTCCCCTCAG TCAAACTTGA GCCAGCCTCT    2940

GGATCGATGT GATCTTATTG CATGTTTCCA TGGGGTGTAC CTATACTTTA AGCCAATCCT    3000

GCTGCATTCA CTGCTAAGTT AAATAAAAAG CCAAGAAGAT TTTGCACTGT GCAGATCCTT    3060

TGCTATCTGA CTTGCATCTC TTCCCCCACC TGTCAGCTAG CCACCTGCTT GTTTGTGTTG    3120

GGATATTTTT TAGCACCTGA AGCACCATCT GAAAGGGGCA CCATTTTCTT CTTCCCTTTG    3180

ATCTCACATA TGCTCCCTAA AAATCCTTAA GTTGTCAATC TGATCCCCAG TGTGAGGTTA    3240

ATGAGCAAAA TTGGTCTTTG GGGCCCTTTT TGTCCAAGCC CCACTGAAAG GCCTCTTCAG    3300

AAAACTATTA TCTTTAAAGC CCTACTTTAA CTCCTTAATT CCAGCATACA GCTAAAACTG    3360

GATGTATATT CTGGCAAGTA AAGGCTGAGG ACTCCTCTTT AATCCTCAGA TCTAGATAAC    3420

TCATGACATT TTATTTGACC AACATAGCAC ATGATGAGAT ATCAAGGTAA TTAAAATAGC    3480

ATGCTTGAAA AAAAAATACG TAATCTGTTT CACCTGTAAC TGTTTAAGCC AATAAACTTT    3540

TCAAAATTTA TGTAATGTGG GGCTTTTATG TAGCACTTTA CGTTTTCATG CTGCTTATTG    3600

TTTTATTCTA CTGAAAAAAA TGAATTTCAA GATTCTCAAC TTTTTTAATT TCAAAAATTG    3660

TTTATTGTTT TGACTATAGG AATACAAAAT TTCCTATTTT GGGAGAATAA GAACTCTTTT    3720

TGTCATTTTT GGCTATGAAT AAACTTTCTG GTCTTTTGAG ACCACCCATT TTTATAGATC    3780

AGAATCAGAA AACAGGTAAA CCTCACTCAC ACATTTGGAC TCATTTGAAC AAAAATCTAG    3840

GCCAAAATAC TGAAAAGCCT ATGTGTTTTT TTAATTGGAA GTATATGTAA GGTTAATGCA    3900

TTTAGTGAAC GTGACTAACA AAGACTAATG TGCACATTAA CAGATGTACT TTTTAAGGTT    3960

TTATGGGAGG CTGTGCATTG CTCAAAAGCT GTTGGGAACG CCTTCTGAAC AGTTGCCTTC    4020

AGAACTAGTT TGAGCTGCTC AATAAAACCA GTGACTTTAC TCATAAAAAA AAAAAAAA    4078
```

(2) INFORMATION FOR SEQ ID NO:4:

(i) SEQUENCE CHARACTERISTICS:
        (A) LENGTH: 318 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Glu Thr Arg Tyr Asn Leu Lys Ser Pro Ala Val Lys Arg Leu Met
  1               5                  10                  15

Lys Glu Ala Ala Glu Leu Lys Asp Pro Thr Asp His Tyr His Ala Gln
             20                  25                  30

Pro Leu Glu Asp Asn Leu Phe Glu Trp His Phe Thr Val Arg Gly Pro
         35                  40                  45

Pro Asp Ser Asp Phe Asp Gly Gly Val Tyr His Gly Arg Ile Val Leu
     50                  55                  60

Pro Pro Glu Tyr Pro Met Lys Pro Pro Ser Ile Ile Leu Leu Thr Ala
 65                  70                  75                  80

Asn Gly Arg Phe Glu Val Gly Lys Lys Ile Cys Leu Ser Ile Ser Gly
                 85                  90                  95

His His Pro Glu Thr Trp Gln Pro Ser Trp Ser Ile Arg Thr Ala Leu
            100                 105                 110

Leu Ala Ile Ile Gly Phe Met Pro Thr Lys Gly Glu Gly Ala Ile Gly
        115                 120                 125

Ser Leu Asp Asn Thr Pro Glu Glu Arg Arg Ala Leu Ala Lys Lys Ser
    130                 135                 140
```

```
Gln Asp Phe Cys Cys Glu Gly Cys Gly Ser Ala Met Lys Asp Val Leu
145                 150                 155                 160

Leu Pro Leu Lys Ser Gly Ser Asp Ser Ser Gln Ala Asp Gln Glu Ala
            165                 170                 175

Lys Glu Leu Ala Arg Gln Ile Ser Phe Lys Ala Glu Val Asn Ser Ser
        180                 185                 190

Gly Asn Thr Ile Ser Glu Ser Asp Leu Asn His Ser Phe Ser Leu Thr
            195                 200                 205

Asp Leu Gln Asp Asp Ile Pro Thr Thr Phe Gln Gly Ala Thr Ala Ser
    210                 215                 220

Thr Ser Tyr Gly Leu Gln Asn Ser Ser Ala Ala Ser Phe His Gln Pro
225                 230                 235                 240

Thr Gln Pro Val Ala Lys Asn Thr Ser Met Ser Pro Arg Gln Arg Arg
                245                 250                 255

Ala Gln Gln Gln Ser Gln Arg Arg Leu Ser Thr Ser Pro Asp Val Ile
            260                 265                 270

Gln Gly His Gln Pro Arg Asp Asn His Thr Asp His Gly Gly Ser Ala
            275                 280                 285

Val Leu Ile Val Ile Leu Thr Leu Ala Leu Ala Ala Leu Ile Phe Arg
290                 295                 300

Arg Ile Tyr Leu Ala Asn Glu Tyr Ile Phe Asp Phe Glu Leu
305                 310                 315
```

(2) INFORMATION FOR SEQ ID NO:5:

(i) SEQUENCE CHARACTERISTICS:
        (A) LENGTH: 1868 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

```
GGCGAGTTCC GGATCCCTGC CTAGCGCGGC CCAACCTTTA CTCCAGAGAT CATGGCTGCC      60

GAGGATGTGG TGGCGACTGG CGCCGACCCA AGCGATCTGG AGAGCGGCGG GCTGCTGCAT     120

GAGATTTTCA CGTCGCCGCT CAACCTGCTG CTGCTTGGCC TCTGCATCTT CCTGCTCTAC     180

AAGATCGTGC GCGGGGACCA GCCGGCGGCC AGCGGCGACA GCGACGACGA CGAGCCGCCC     240

CCTCTGCCCC GCCTCAAGCG GCGCGACTTC ACCCCCGCCG AGCTGCGGCG CTTCGACGGC     300

GTCCAGGACC CGCGCATACT CATGGCCATC AACGGCAAGG TGTTCGATGT GACCAAAGGC     360

CGCAAATTCT ACSGGCCCGA RGGGCCGTAT GGGGTCTTTG CTGGAAGAGA TGCATCCAGG     420

GGCCTTGCCA CATTTTGCCT GGATAAGGAA GCACTGAAGG ATGAGTACGA TGACCTTTCT     480

GACCTCACTG CTGCCCAGCA GGAGACTCTG AGTGACTGGG AGTCTCAGTT CACTTTCAAG     540

TATCATCACG TGGGCAAACT GCTGAAGGAG GGGGAGGAGC CCACTGTGTA CTCAGATGAG     600

GAAGAACCAA AGATGAGAG TGCCCGGAAA ATGATTAAAG CATTCAGTG GAAGTATATC       660

TATTTTTGTA TTTTGCAAAA TCATTTGTAA CAGTCCACTC TGTCTTTAAA ACATAGTGAT     720

TACAATATTT AGAAAGTTTT GAGCACTTGC TATAAGTTTT TTAATTAACA TCACTAGTGA     780

CACTAATAAA ATTAACTTCT TAGAATGCAT GATGTGTTTG TGTGTCACAA ATCCAGAAAG     840

TGAACTGCAG TGCTGTAATA CACATGTTAA TACTGTTTTT CTTCTATCTG TAGTTAGTAC     900

AGGATGAATT TAAATGTGTT TTTCCTGAGA GACAAGGAAG ACTTGGGTAT TTCCCAAAAC     960

AGGTAAAAAT CTTAAATGTG CACCAAGAGC AAAGGATCAA CTTTTAGTCA TGATGTTCTG    1020
```

-continued

```
TAAAGACAAC AAATCCCTTT TTTTTTCTCA ATTGACTTAA CTGCATGATT TCTGTTTTAT    1080

CTACCTCTAA AGCAAATCTG CAGTGTTCCA AAGACTTTGG TATGGATTAA GCGCTGTCCA    1140

GTAACAAAAT GAAATCTCAA AACAGAGCTC AGCTGCAAAA AAGCATATTT TCTGTGTTTC    1200

TGGACTGCAC TGTTGTCCTT GCCCTCACAT AGACACTCAG ACACCCTCAC AAACACAGTA    1260

GTCTATAGTT AGGATTAAAA TAGGATCTGA ACATTCAAAA GAAAGCTTTG GAAAAAAGA     1320

GCTGGCTGGC CTAAAAACCT AAATATATGA TGAAGATTGT AGGACTGTCT TCCCAAGCCC    1380

CATGTTCATG GTGGGCAAT GGTTATTTGG TTATTTTACT CAATTGGTTA CTCTCATTTG     1440

AAATGAGGGA GGGACATACA GAATAGGAAC AGGTGTTTGC TCTCCTAAGA GCCTTCATGC    1500

ACACCCCTGA ACCACGAGGA AACAGTACAG TCGCTAGTCA AGTGGTTTTT AAAGTAAAGT    1560

ATATTCATAA GGTAACAGTT ATTCTGTTGT TATAAAACTA TACCCACTGC AAAAGTAGTA    1620

GTCAAGTGTC TAGGTCTTTG ATATTGCTCT TTTGGTTAAC ACTAAGCTTA AGTAGACTAT    1680

ACAGTTGTAT GAATTTGTAA AAGTATATGA ACACCTAGTG AGATTTCAAA CTTGTAATTG    1740

TGGTTAAATA GTCATTGTAT TTTCTTGTGA ACTGTGTTTT ATGATTTTAC CTCAAATCAG    1800

AAAACAAAAT GATGTGCTTT GGTCAGTTAA TAAAAATGGT TTTACCCACT AAAAAAAAAA    1860

AAAAAAAA                                                             1868
```

(2) INFORMATION FOR SEQ ID NO:6:

(i) SEQUENCE CHARACTERISTICS:
        (A) LENGTH: 195 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
        35                  40                  45

Asp Gln Pro Ala Ala Ser Gly Asp Ser Asp Asp Glu Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Xaa Pro Glu Gly Pro
            100                 105                 110

Tyr Gly Val Phe Ala Gly Arg Asp Ala Ser Arg Gly Leu Ala Thr Phe
        115                 120                 125

Cys Leu Asp Lys Glu Ala Leu Lys Asp Glu Tyr Asp Asp Leu Ser Asp
    130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Pro Lys Asp Glu Ser Ala Arg
            180                 185                 190
```

Lys Asn Asp
    195

(2) INFORMATION FOR SEQ ID NO:7:

(i) SEQUENCE CHARACTERISTICS:
        (A) LENGTH: 1428 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
AACCGTTGCT GGGTGTCCCA GGGCCTGAGG CAGGACGGTA CTCCGCTGAC ACCTTCCCTT    60
TCGGCCTTGA GGTTCCCAGC CTGGTGGCCC CAGGACGTTC CGGTCGCATG GCAGAGTGCT   120
ACGGACGACG CCTATGAAGC CCTTAGTCCT TCTAGTTGCG CTTTTGCTAT GGCCTTCGTC   180
TGTGCCGGCT TATCCGAGCA TAACTGTGAC ACCTGATGAA GAGCAAAACT TGAATCATTA   240
TATACAAGTT TTAGAGAACC TAGTACGAAG TGTTCCCTCT GGGGAGCCAG GTCGTGAGAA   300
AAAATCTAAC TCTCCAAAAC ATGTTTATTC TATAGCATCA AAGGGATCAA AATTTAAGGA   360
GCTAGTTACA CATGGAGACG CTTCAACTGA GAATGATGTT TTAACCAATC CTATCAGTGA   420
AGAAACTACA ACTTTCCCTA CAGGAGGCTT CACACCGGAA ATAGGAAAGA AAAACACAC    480
GGAAAGTACC CCATTCTGGT CGATCAAACC AAACAATGTT TCCATTGTTT TGCATGCAGA   540
GGAACCTTAT ATTGAAAATG AAGAGCCAGA GCCAGAGCCG GAGCCAGCTG CAAAACAAAC   600
TGAGGCACCA AGAATGTTGC CAGTTGTTAC TGAATCATCT ACAAGTCCAT ATGTTACCTC   660
ATACAAGTCA CCTGTCACCA CTTTAGATAA GAGCACTGGC ATTGAGATCT CTACAGAATC   720
AGAAGATGTT CCTCAGCTCT CAGGTGAAAC TGCGATAGAA AAACCCGAAG AGTTTGGAAA   780
GCACCCAGAG AGTTGGAATA ATGATGACAT TTTGAAAAAA ATTTTAGATA TTAATTCACA   840
AGTGCAACAG GCACTTCTTA GTGACACCAG CAACCCAGCA TATAGAGAAG ATATTGAAGC   900
CTCTAAAGAT CACCTAAAAC GAAGCCTTGY TCTAGCAGCA GCAGCAGAAC ATAAATTAAA   960
AACAATGTAT AAGTCCCAGT TATTGCCAGT AGGACGAACA AGTAATAAAA TTGATGACAT  1020
CGAAACTGTT ATTAACATGC TGTGTAATTC TAGATCTAAA CTCTATGAAT ATTTAGATAT  1080
TAAATGTGTT CCACCAGAGA TGAGAGAAAA AGCTGCTACA GTATTCAATA CATTAAAAAA  1140
TATGTGTAGA TCAAGGAGAG TCACAGCCTT ATTAAAAGTT TATTAAACAA TAATATAAAA  1200
ATTTTAAACC TACTTGATAT TCCATAACAA AGCTGATTTA AGCAAACTGC ATTTTTTCAC  1260
AGGAGAAATA ATCATATTCG TAATTTCAAA AGTTGTATAA AAATATTTTC TATTGTAGTT  1320
CAAATGTGCC AACATCTTTA TGTGTCATGT GTTATGAACA ATTTTCATAT GCACTAAAAA  1380
CCTAATTTAA AATAAAATTT TGGTTCAGGA AAAAAAAAA AAAAAAAA                 1428
```

(2) INFORMATION FOR SEQ ID NO:8:

(i) SEQUENCE CHARACTERISTICS:
        (A) LENGTH: 350 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

Met Lys Pro Leu Val Leu Leu Val Ala Leu Leu Leu Trp Pro Ser Ser
1               5                   10                  15

```
Val Pro Ala Tyr Pro Ser Ile Thr Val Thr Pro Asp Glu Glu Gln Asn
            20                  25                  30

Leu Asn His Tyr Ile Gln Val Leu Glu Asn Leu Val Arg Ser Val Pro
            35                  40                  45

Ser Gly Glu Pro Gly Arg Glu Lys Lys Ser Asn Ser Pro Lys His Val
 50                  55                  60

Tyr Ser Ile Ala Ser Lys Gly Ser Lys Phe Lys Glu Leu Val Thr His
 65                  70                  75                  80

Gly Asp Ala Ser Thr Glu Asn Asp Val Leu Thr Asn Pro Ile Ser Glu
            85                  90                  95

Glu Thr Thr Thr Phe Pro Thr Gly Gly Phe Thr Pro Glu Ile Gly Lys
            100                 105                 110

Lys Lys His Thr Glu Ser Thr Pro Phe Trp Ser Ile Lys Pro Asn Asn
            115                 120                 125

Val Ser Ile Val Leu His Ala Glu Gly Pro Tyr Ile Glu Asn Glu Glu
            130                 135                 140

Pro Glu Pro Glu Pro Glu Pro Ala Ala Lys Gln Thr Glu Ala Pro Arg
145                 150                 155                 160

Met Leu Pro Val Val Thr Glu Ser Ser Thr Ser Pro Tyr Val Thr Ser
            165                 170                 175

Tyr Lys Ser Pro Val Thr Thr Leu Asp Lys Ser Thr Gly Ile Glu Ile
            180                 185                 190

Ser Thr Glu Ser Glu Asp Val Pro Gln Leu Ser Gly Glu Thr Ala Ile
            195                 200                 205

Glu Lys Pro Glu Glu Phe Gly Lys His Pro Glu Ser Trp Asn Asn Asp
 210                 215                 220

Asp Ile Leu Lys Lys Ile Leu Asp Ile Asn Ser Gln Val Gln Gln Ala
225                 230                 235                 240

Leu Leu Ser Asp Thr Ser Asn Pro Ala Tyr Arg Glu Asp Ile Glu Ala
            245                 250                 255

Ser Lys Asp His Leu Lys Arg Ser Leu Xaa Leu Ala Ala Ala Ala Glu
            260                 265                 270

His Lys Leu Lys Thr Met Tyr Lys Ser Gln Leu Leu Pro Val Gly Arg
            275                 280                 285

Thr Ser Asn Lys Ile Asp Asp Ile Glu Thr Val Ile Asn Met Leu Cys
            290                 295                 300

Asn Ser Arg Ser Lys Leu Tyr Glu Tyr Leu Asp Ile Lys Cys Val Pro
305                 310                 315                 320

Pro Glu Met Arg Glu Lys Ala Ala Thr Val Phe Asn Thr Leu Lys Asn
            325                 330                 335

Met Cys Arg Ser Arg Arg Val Thr Ala Leu Leu Lys Val Tyr
            340                 345                 350

(2) INFORMATION FOR SEQ ID NO:9:

(i) SEQUENCE CHARACTERISTICS:
        (A) LENGTH: 3742 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:9:

GATCCCCACC ACACCACCAG CCCGGCCGCA CGGGGCACTG AGCCGGGTGC TGAGCACCGG      60

AGGCCCCGCC GAGGCCGGGA CTCAGGACCT GCAGAGAAAC GCCTCCTGAT TTTGTCTTAC    120
```

```
AATGGAACTT AAAAAGTCGC CTGACGGTGG ATGGGGCTGG GTGATTGTGT TTGTCTCCTT    180

CCTTACTCAG TTTTTGTGTT ACGGATCCCC ACTAGCTGTT GGAGTCCTGT ACATAGAATG    240

GCTGGATGCC TTTGGTGAAG GAAAAGGAAA ACAGCCTGG GTTGGATCCC TGGCAAGTGG     300

AGTTGGCTTG CTTGCAAGTC CTGTCTGCAG TCTCTGTGTC TCATCTTTTG GAGCAAGACC    360

TGTCACAATC TTCAGTGGCT TCATGGTGGC TGGAGGCCTG ATGTTGAGCA GTTTTGCTCC    420

CAATATCTAC TTTCTGTTTT TTTCCTATGG CATTGTTGTA GGTGCTCCAA ATATTGCTGT    480

TTGGAGAAAT CTGCACCTTA ATAAGAGCAG TTATTTGTGA GAAAAAAAAA AGACAAGAAT    540

ATATATGAGA TGGGTGTGAC GAAGATCCAG TCTCTCTACA TGAAGACCAG ACTGATTGCT    600

CCAGTCTCAG AGATGAAAAC AATAAAGAGA ACTACCCCGA CGCAGGGGCT CTGGTAGAAG    660

AGACGCGCCG CCCTCTTGGG AGCCGCAGCA GCAGAATGTA GAGGCGACCG TGCTGGTGGA    720

CAGCGTATTG CGACCCAGCA TGGGCAACTT CAAGTCCAGG AAGCCCAAGT CCATCTTCAA    780

AGCGGAGAGC GGGAGGAGCC ACGGAGAAAG TCAGGAGACA GAGCATGTGG TATCCAGCCA    840

GTCAGAGTGT CAGGTGAGAG CAGGAACACC AGCTCATGAG AGTCCACAAA ACAATGCCTT    900

CAAGTGCCAA GAAACAGTGC GACTTCAACC AAGAATAGAC CAGAGGACTG CCATTTCGCC    960

AAAGGATGCT TTTGAAACTC GGCAGGACTT AAATGAGGAA GAAGCTGCTC AGGTGCATGG    1020

AGTCAAGGAC CCGGCGCCAG CATCAACCCA GAGCGTGCTT GCCGATGGGA CAGATTCTGC    1080

AGACCCCTCA CCAGTCCACA AAGATGGGCA GAATGAGGCC GACAGTGCAC CAGAAGACCT    1140

CCACTCTGTG GGGACCAGCA GGCTGCTCTA TCACATCACT GATGGTGATA ACCCACTGCT    1200

GTCGCCACGA TGCTCCATCT TCAGCCAAAG CCAGAGATTC AACTTAGACC CCGAGTCAGC    1260

CCCATCTCCA CCCAGCACTC AGCAGTTTAT GATGCCGCGG AGTTCTTCAC GCTGCAGCTG    1320

TGGAGATGGC AAGGAGCCAC AGACCATCAC CCAGCTCACC AAGCACATCC AGAGCCTCAA    1380

GCGGAAAATT CGGAAATTTG AAGAAAAATT TGAACAAGAA AAGAAATACC GGCCTTCACA    1440

TGGTGACAAG ACTTCTAATC CTGAAGTCCT GAAATGGATG AATGATTTGG CTAAAGGTCG    1500

TAAACAGCTC AAAGAACTAA AGCTAAAGCT GTCAGAAGAA CAAGGGAGTG CTCCCAAAGG    1560

TCCACCTAGA AACCTGTTGT GTGAGCAACC CACAGTCCCC AGAGAAAATG GGAAACCGGA    1620

AGCTGCGGGC CCGGAGCCAA GCTCCTCTGG AGAAGAGACT CCAGATGCTG CCTTGACATG    1680

CCTGAAGGAG AGAAGAGAGC AACTTCCTCC CCAGGAGGAT TCTAAGGTAA CTAAGCAAGA    1740

CAAGAACCTC ATAAAGCCGC TTTATGACCG ATACAGAATT ATCAAGCAAA TCTTGTCAAC    1800

ACCTTCCCTT ATTCCAACAA TTCAGGAGGA AGAGGACTCT GATGAAGACC GTCCACAGGG    1860

AAGCCAACAA CCTTCTTTGG CAGATCCAGC ATCTCACCTT CCTGTTGGTG ACCACCTCAC    1920

CTACTCTAAT GAGACTGAGC CTGTTAGGGC CCTTTTACCA GATGAAAAGA AAGAAGTAAA    1980

ACCACCAGCT CTCTCCATGT CTAATTTACA TGAGGCTACC ATGCCTGTAC TTCTTGACCA    2040

TCTCCGAGAA ACTAGGGCTG ACAAGAAGAG ACTGCGGAAA GCCTTAAGAG AATTTGAAGA    2100

ACAGTTTTTT AAACAAACAG GAAGAAGTCC ACAAAAGGAA GATAGGATAC CAATGGCAGA    2160

TGAGTATTAT GAATATAAGC ACATAAAAGC CAAACTGAGA CTATTAGAGG TCCTCATCAG    2220

CAAGCAAGAT GTGGCCAAAA CTATTTGAGG TTCAGGAAAT GTTATGATCA CTTTCACCCA    2280

TGATATAAAG TAAAGTTTAT TTTCCTCTGC CATCCTTGCT AAGTAGTTTT GACACAATGA    2340

AAATGGAAGC ACTTTAGTGG TAGTATTAGC TGTTTTTAAG AAGGAATAGC AAGTTTAATT    2400

ATATACAAGG AGAAGGGATT TAAACGGGGG GAAGAATACA ACAGGTAGCC ATATAATTGG    2460

GAAAAAATTC AGTGTCCTCC ATGCCAAGCA GAAAACTCAT AGTCAATACA AGTATTTTTA    2520
```

-continued

```
AAAATGTCTA ATATTTTATC AAATCTAAAT AACATAGCTA GGACACTTGT TAGGGAAAGT    2580

TTATTTAGTA TCCAAAGACT GTTTATGTTG ATGTATGGAA AAGAGCATGA TTTTAAAAAA    2640

TCAATCATAG GAGGAAAAGA AATTCGCTTT TCAAGTAGGA AGGAATACAG CTAGCAAGAA    2700

AGCAATTTAT TTGAAACTTC TAATGGATTT TTGAGTGATA AAACATTTAC TACCTTGTCC    2760

TTTAAGTCTG CTAGGCTCTC AGTACCCTAA AATAAACTAG ATTGTGTTGC TATTTTTTTT    2820

CTTTCTCTAT AAAAATAACA CATTATTTTA TCCGTTATTT GAAATTTTAC ATTTCTGGTT    2880

ACCAAAGTTC ATTCTGATAG CATGTACTTT GTGAATTATT ATCTTTGTCT ATAACTGACA    2940

GATGTTTATA TTAAAATAAA ATATTGTATT AAAAATTTAA AATAGGTATT TTGGATAGAT    3000

ATGTGTCTGT AGTATATAAT CTAATGTGTC CATAGTATTA TTGCTAATCT TTTGGTTTAC    3060

TATAAGATGA TATAACTATT TTTTCATTGG GAATATACAT TTTTCTTAAT GTTCCAACAT    3120

CTATACTTTG TAAAGTCAAA ACATTTCCCA TGAGCTGTAG TTATTCATCC TTCTGTACAA    3180

AATGAAAAGT TTGGAAATTG TTTGCCCTGA TACCTTGAAA AAGAAGCCAG AATATTTATT    3240

TGCTTCATCA ACTTCAGTGT ATATCATTTT GTGTTATTTT ATACGAAAAC ATGTTTATTA    3300

TTTTCATTTT TGTAAAAGGA AGTAAAAGGT CAACATTTTC TCTCATGTAC CAACCTTGTT    3360

TGTATTTCTA TTTTTCTGTA ATGTTTAAGT ATGGATGTTG GAAGAAATTC AACATTCTCT    3420

TATAGTTTGG ATGGGAAGAC TATTGACTAT TTCAGAAACA GACTTATTTC AGAGGCTTAT    3480

TGTTTTCTCT GTATTTACCT AATATTTTAT AACTTTTATG AATCAGAATA ATGTCCTTCA    3540

TAAATTTGTT TAATTGAAGT CATCTACTTY TAACAGGACA GATACACAAC TATTTGAGGT    3600

TTACAAATTA CATCTTTGAT AAGGGAAATG GTTTCGTGAC ATGTACACAG TTGCTATTAA    3660

AATGTAACTC TATATATTCT ATATGATTGT AAATATTTTA TACAACAATA CAAATAAAAT    3720

ATTTTTCTAT TAAAAAAAAA AA                                             3742
```

(2) INFORMATION FOR SEQ ID NO:10:

(i) SEQUENCE CHARACTERISTICS:
        (A) LENGTH: 502 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Gly Asn Phe Lys Ser Arg Lys Pro Lys Ser Ile Phe Lys Ala Glu
1               5                   10                  15

Ser Gly Arg Ser His Gly Glu Ser Gln Glu Thr Glu His Val Val Ser
            20                  25                  30

Ser Gln Ser Glu Cys Gln Val Arg Ala Gly Thr Pro Ala His Glu Ser
        35                  40                  45

Pro Gln Asn Asn Ala Phe Lys Cys Gln Glu Thr Val Arg Leu Gln Pro
    50                  55                  60

Arg Ile Asp Gln Arg Thr Ala Ile Ser Pro Lys Asp Ala Phe Glu Thr
65                  70                  75                  80

Arg Gln Asp Leu Asn Glu Glu Glu Ala Ala Gln Val His Gly Val Lys
                85                  90                  95

Asp Pro Ala Pro Ala Ser Thr Gln Ser Val Leu Ala Asp Gly Thr Asp
            100                 105                 110

Ser Ala Asp Pro Ser Pro Val His Lys Asp Gly Gln Asn Glu Ala Asp
        115                 120                 125

Ser Ala Pro Glu Asp Leu His Ser Val Gly Thr Ser Arg Leu Leu Tyr
```

```
              130                 135                 140
His Ile Thr Asp Gly Asp Asn Pro Leu Leu Ser Pro Arg Cys Ser Ile
145                 150                 155                 160

Phe Ser Gln Ser Gln Arg Phe Asn Leu Asp Pro Glu Ser Ala Pro Ser
                165                 170                 175

Pro Pro Ser Thr Gln Gln Phe Met Met Pro Arg Ser Ser Ser Arg Cys
                180                 185                 190

Ser Cys Gly Asp Gly Lys Glu Pro Gln Thr Ile Thr Gln Leu Thr Lys
                195                 200                 205

His Ile Gln Ser Leu Lys Arg Lys Ile Arg Lys Phe Glu Glu Lys Phe
    210                 215                 220

Glu Gln Glu Lys Lys Tyr Arg Pro Ser His Gly Asp Lys Thr Ser Asn
225                 230                 235                 240

Pro Glu Val Leu Lys Trp Met Asn Asp Leu Ala Lys Gly Arg Lys Gln
                245                 250                 255

Leu Lys Glu Leu Lys Leu Lys Leu Ser Glu Glu Gln Gly Ser Ala Pro
                260                 265                 270

Lys Gly Pro Pro Arg Asn Leu Leu Cys Glu Gln Pro Thr Val Pro Arg
                275                 280                 285

Glu Asn Gly Lys Pro Glu Ala Ala Gly Pro Glu Pro Ser Ser Ser Gly
                290                 295                 300

Glu Glu Thr Pro Asp Ala Ala Leu Thr Cys Leu Lys Glu Arg Arg Glu
305                 310                 315                 320

Gln Leu Pro Pro Gln Glu Asp Ser Lys Val Thr Lys Gln Asp Lys Asn
                325                 330                 335

Leu Ile Lys Pro Leu Tyr Asp Arg Tyr Arg Ile Ile Lys Gln Ile Leu
                340                 345                 350

Ser Thr Pro Ser Leu Ile Pro Thr Ile Gln Glu Glu Glu Asp Ser Asp
                355                 360                 365

Glu Asp Arg Pro Gln Gly Ser Gln Gln Pro Ser Leu Ala Asp Pro Ala
                370                 375                 380

Ser His Leu Pro Val Gly Asp His Leu Thr Tyr Ser Asn Glu Thr Glu
385                 390                 395                 400

Pro Val Arg Ala Leu Leu Pro Asp Glu Lys Lys Glu Val Lys Pro Pro
                405                 410                 415

Ala Leu Ser Met Ser Asn Leu His Glu Ala Thr Met Pro Val Leu Leu
                420                 425                 430

Asp His Leu Arg Glu Thr Arg Ala Asp Lys Lys Arg Leu Arg Lys Ala
                435                 440                 445

Leu Arg Glu Phe Glu Glu Gln Phe Phe Lys Gln Thr Gly Arg Ser Pro
                450                 455                 460

Gln Lys Glu Asp Arg Ile Pro Met Ala Asp Glu Tyr Tyr Glu Tyr Lys
465                 470                 475                 480

His Ile Lys Ala Lys Leu Arg Leu Leu Glu Val Leu Ile Ser Lys Gln
                485                 490                 495

Asp Val Ala Lys Thr Ile
                500

(2) INFORMATION FOR SEQ ID NO:11:

(i) SEQUENCE CHARACTERISTICS:
        (A) LENGTH: 2061 base pairs
        (B) TYPE: nucleic acid
        (C) STRANDEDNESS: double
        (D) TOPOLOGY: linear
```

(ii) MOLECULE TYPE: cDNA (xi) SEQUENCE DESCRIPTION: SEQ ID NO:11:

| | | | | | |
|---|---|---|---|---|---|
| AATCGTCGGG | AAGTGTTTTT | GAGAAGTCTC | GGTCGGTAAG | GGAAGTCTTC | CAAGTCCGTG | 60 |
| CAGCACTAAC | GTATTGGCAC | CTGCCTCCTC | TTCGGCCACC | CCCCAGATGA | GGCAGCTGTG | 120 |
| ACTGTGTCAA | GGGAAGCCAC | GACTCTGACC | ATAGTCTTCT | CTCAGCTTCC | ACTGCCGTCT | 180 |
| CCACAGGTGG | GCTTCACTTT | CGTGGAATCC | TTGGGCTGCC | GAGTTACACC | TTAGGAATCC | 240 |
| TCTAATTTTC | TTTCCACCTT | TTGCACGCAC | GCCAGGAGAT | TTCTTTTCTT | CATCTGTCCA | 300 |
| GTGAGGTTAC | CGTTTTTACT | TCACAGGATT | GTTGTGAAGA | CCGAATTGCC | AAGTGCAGTT | 360 |
| CCTGGCGCGG | AGTAGGCAGG | TCTTATAAAT | ATTGGTTCAG | TCTGAAGTTT | ATCCTGGTTG | 420 |
| TTTCCCTTCT | GATAATTTTT | TAAGCACTTT | TTATTTGCTG | GGTGTTTTCA | CATACTTGAT | 480 |
| GGCCATCTGA | CAGATGAGCA | AGGAGGCTCA | GAAGCTCAGC | TTAAGATTTA | AAAAAAAGCA | 540 |
| GGGGGGCTAG | AATTTAAATC | AAGGTCTATC | TGATGTCTAA | GCTACCTATT | CTGTTATACT | 600 |
| GCATAATACC | CTTTTTATAT | TATTTTTTAT | ATTTAATCAG | TAACATATGT | AGATAGTACA | 660 |
| AAATTCAACA | GATATCAAAG | TGTGTTAAGT | TTACCTTTCC | ACCCACTTTC | TCATTTTTGT | 720 |
| CTCCCCCAGT | TCCTTTTGCA | TTATTCCACG | TATATTCTGT | GCATATATAC | ATTCATATAC | 780 |
| ATTTATCTGT | ATGTGTCAGC | TTCTTTTTAC | ACAAATGATA | CATAAACACT | GTTCTGGACC | 840 |
| TTCCAACTTA | GAATTACTGC | AAACAGTGTC | GTGATGAATT | ACCTAATTCT | GTGTATGTGT | 900 |
| GTATATTGGT | AGAAAAAATT | CCCGGAAGTA | GAATTGCTAG | AACAAAGATT | TATGCATTTT | 960 |
| AAATATTCCT | TTATTATAAA | ACTAATGAAA | GTAAACATGT | TGGCTATGAC | CACGTATGCT | 1020 |
| CTATGCTCAG | TTTTTCTAGA | GTTGTGTATG | CTTAATATAG | GAGTAAGATT | CTTTTAAAAT | 1080 |
| GGTATATTCA | TTGCCTTATT | TGATTTTCAT | AGTCAATCGT | TTTAATTTTT | CAGTCTACAT | 1140 |
| ATATAGGTGT | TTGGAAAGGA | TATAAATATC | TTCTGCTGCA | TGTACCTACA | GTGATAAACT | 1200 |
| CTCTCCTCCT | ACATACCTTT | GAGATTTTTT | TTTTTTTTTT | GAGACAGAGT | CTCTCTCTGT | 1260 |
| CACTCAGGCT | GGAGTGCAGT | GGCACAGTCT | GGGCTCACTG | CATCCTCTGC | CTACCGGGTT | 1320 |
| CAAGCAGTTC | TCCTGCCTCA | GCCTCTCGAG | TAGCTGGGAT | TACAGGCACC | TGTCACCACG | 1380 |
| CCTGGCTAAT | TTTTGTATTT | TTAGTTGAGA | CGGGGTTTCA | CCATGTTGGG | CAGGCTAGTC | 1440 |
| TCGAACTCCT | GACCTCAAGT | GATCCGCCTG | CCTTGGCCTC | CCACAGTGTT | GGGATTACAG | 1500 |
| GTGTGAGCCA | CCGTGCCTGG | CCTACCTTTG | AGATTTGTGA | TGAGGAAACA | AGAGATGAAT | 1560 |
| TGTATGAGAG | CACTTCAAAA | GATTCATGGA | AAATACTTAT | TTCAAAAGA | GTAGTTAATA | 1620 |
| TTACCTTATT | TTTCTTATCT | GCTAACCCCT | TTCTTTCAAA | TGCACTTAGG | ACTTGCTGCT | 1680 |
| AAAACTCACT | GCAAGTAAGA | TACCACAAGG | AGGCAGCATA | GAACTGATTT | TCTATACATG | 1740 |
| CTCAGGACAG | TAGTTTCACT | CATAGATGAA | AAGTTAGAAT | TTGGATTTAT | TTGAAATATA | 1800 |
| TACAAATATT | CAAGTATATA | CATATATTCA | AATAAATACA | TATATGTATA | TATGTGTGTA | 1860 |
| TATACACACA | TACATACACA | TGAATCATCA | TTGCCTTCTT | GAGATCTCAC | CACTTTAGTC | 1920 |
| CTACTAAGAT | GGGTGGTTGT | TGGTTTTTTT | TTGTTGTTGT | TGTTGTTTTT | TAAATTCCAA | 1980 |
| TCTGTATGGA | ATGATACTTT | AATAAAATTA | TGTGCTCGGA | TGTTGAATAA | ATGTCAAATT | 2040 |
| GCCATAAAAA | AAAAAAAAA | A | | | | 2061 |

(2) INFORMATION FOR SEQ ID NO:12:

(i) SEQUENCE CHARACTERISTICS:
  (A) LENGTH: 41 amino acids
  (B) TYPE: amino acid (C) STRANDEDNESS:
        (D) TOPOLOGY: linear (ii) MOLECULE TYPE: protein (xi) SEQUENCE DESCRIPTION: SEQ ID NO:12:

```
Met His Phe Lys Tyr Ser Phe Ile Ile Lys Leu Met Lys Val Asn Met
 1               5                  10                  15

Leu Ala Met Thr Thr Tyr Ala Leu Cys Ser Val Phe Leu Glu Leu Cys
            20                  25                  30

Met Leu Asn Ile Gly Val Arg Phe Phe
            35                  40
```

(2) INFORMATION FOR SEQ ID NO:13:

(i) SEQUENCE CHARACTERISTICS:
        (A) LENGTH: 1772 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

| | | | | | |
|---|---|---|---|---|---|
| CGGAAGCGGG | TCCCGCAGGT | CGCCACGGTT | GGGGGAAACG | CGGCGGACGC | CGCCCCCGTC | 60 |
| CCGAAGGGGA | CTCGAAAATG | TACAGCCAGC | GGTTTGGCAC | CGTACAGCGG | GAGGTTAAGG | 120 |
| GCCCCACCCC | CAAAGTGGTG | ATCGTGAGAT | CCAAGCCTCC | TAAAGGCCAA | GGAGCTGAGC | 180 |
| ACCATCTAGA | AAGAATCCGA | CGCAGCCATC | AGAAGCATAA | TGCTATTTTG | GCTTCCATTA | 240 |
| AGTCAAGTGA | GCGGGATCGC | TTGAAAGCTG | AGTGGGACCA | GCACAATGAC | TGCAAGATTT | 300 |
| TGGACAGCCT | TGTGCGAGCA | AGAATCAAGG | ATGCTGTGCA | AGGGTTTATC | ATTAACATTG | 360 |
| AAGAAAGACG | AAATAAGCTA | CGTGAGCTTT | TAGCATTAGA | AGAAAATGAG | TATTTTACAG | 420 |
| AAATGCAATT | GAAGAAAGAA | ACCATTGAGG | AGAAAAAAGA | TAGGATGAGA | GAGAAAACTA | 480 |
| AATTACTAAA | AGAAGAAGAAT | GAAAAGAGA | GGCAGGATTT | TGTGGCTGAA | AAGCTAGACC | 540 |
| AGCAATTCAG | GGAACGCTGT | GAGGAGCTCC | GTGTTGAATT | GTTATCTATC | CATCAGAAGA | 600 |
| AGGTGTGTGA | GGAGCGGAAA | GCACAGATTG | CATTTAATGA | GGAGCTGAGC | AGGCAAAAGC | 660 |
| TGGTGGAAGA | GCAGATGTTC | TCCAAACTCT | GGGAGGAAGA | CCGATTAGCC | AAGGAAAAGC | 720 |
| GAGAAGCCCA | GAGGCGAGG | AGACAGAAAG | AGCTGATGGA | GAACACACGC | CTGGGGCTGA | 780 |
| ATGCCCAGAT | CACCAGCATC | AAGGCACAAA | GGCAGGCGAC | ACAGCTGCTG | AAGGAAGAGG | 840 |
| AGGCACGCCT | TGTGGAAAGT | AACAACGCAC | AGATTAAACA | TGAGAATGAA | CAGGATATGC | 900 |
| TAAAGAAACA | GAAGGCAAAG | CAGGAAACTA | GGACCATTTT | GCAAAAAGCC | CTACAAGAGA | 960 |
| GGATAGAACA | TATTCAGCAG | GAATACAGAG | ACGAACAGGA | CTTGAACATG | AAGCTCGTGC | 1020 |
| AAAGGGCCCT | TCAAGACTTA | CAGGAAGAGG | CAGATAAAAA | GAAACAAAAA | AGAGAAGATA | 1080 |
| TGATAAGAGA | ACAGAAGATA | TACCATAAAT | ATTTGGCACA | GAGACGTGAG | GAAGAAAAAG | 1140 |
| CTCAGGAGAA | AGAATTTGAC | AGAATATTAG | AGGAAGACAA | GGCAAAGAAG | TTGGCTGAGA | 1200 |
| AGGACAAGGA | GCTGAGACTT | GAAAAGGAGG | CAAGGAGACA | GCTTGTGGAT | GAGGTCATGT | 1260 |
| GTACAAGAAA | ACTTCAAGTT | CAAGAAAAGT | TGCAACGAGA | AGCTAAAGAA | CAGGAAGAAC | 1320 |
| GTGCTATGGA | ACAGAAACAC | ATAAATGAAA | GTCTTAAAGA | ACTTAACTGT | GAAGAGAAGG | 1380 |
| AGAATTTTGC | AAGACGCCAA | CGTTTAGCCC | AGGAGTACAG | GAAGCAACTT | CAGATGCAAA | 1440 |
| TCGCCTACCA | GCAGCAGTCC | CAAGAAGCAG | AGAAGGAAGA | GAAACGCCGA | GAGTTTGAAG | 1500 |
| CAGGTGTAGC | AGCAAACAAG | ATGTGTTTGG | ACAAGGTCCA | GGAGGTCCTG | TCCACCCATC | 1560 |

```
AAGTGCTGCC TCAAAACATT CATCCCATGC GCAAGGCATG CCCCAGTAAG CTTCCACCGT      1620

AGTTCCGTGA GCATCAATAT ATCTTTTCTT GGTCTTTTAA TATTTTTAAC TACAGTATGC      1680

TTGTATGCTT CTTTTAACTC CTGGATAAAC TTTTCTTTTT TCCCTGAAAA AAAAAAAAA       1740

AAAAAAAAAA AAAAAAAAAA AAAAAAAAA AA                                     1772

(2) INFORMATION FOR SEQ ID NO:14:

(i) SEQUENCE CHARACTERISTICS:
        (A) LENGTH: 514 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:
```

| | | | | | | | | | | | | | | |
|---|---|---|---|---|---|---|---|---|---|---|---|---|---|---|
| Met | Tyr | Ser | Gln | Arg | Phe | Gly | Thr | Val | Gln | Arg | Glu | Val | Lys | Gly | Pro |
| 1 | | | | 5 | | | | | 10 | | | | | 15 | |
| Thr | Pro | Lys | Val | Val | Ile | Val | Arg | Ser | Lys | Pro | Pro | Lys | Gly | Gln | Gly |
| | | | 20 | | | | | 25 | | | | | 30 | | |
| Ala | Glu | His | His | Leu | Glu | Arg | Ile | Arg | Arg | Ser | His | Gln | Lys | His | Asn |
| | | | | 35 | | | | | 40 | | | | | 45 | |
| Ala | Ile | Leu | Ala | Ser | Ile | Lys | Ser | Ser | Glu | Arg | Asp | Arg | Leu | Lys | Ala |
| | | | 50 | | | | | 55 | | | | | 60 | | |
| Glu | Trp | Asp | Gln | His | Asn | Asp | Cys | Lys | Ile | Leu | Asp | Ser | Leu | Val | Arg |
| 65 | | | | | 70 | | | | | 75 | | | | | 80 |
| Ala | Arg | Ile | Lys | Asp | Ala | Val | Gln | Gly | Phe | Ile | Ile | Asn | Ile | Glu | Glu |
| | | | | 85 | | | | | 90 | | | | | 95 | |
| Arg | Arg | Asn | Lys | Leu | Arg | Glu | Leu | Leu | Ala | Leu | Glu | Glu | Asn | Glu | Tyr |
| | | | 100 | | | | | 105 | | | | | 110 | | |
| Phe | Thr | Glu | Met | Gln | Leu | Lys | Lys | Glu | Thr | Ile | Glu | Glu | Lys | Lys | Asp |
| | | | | 115 | | | | | 120 | | | | | 125 | |
| Arg | Met | Arg | Glu | Lys | Thr | Lys | Leu | Leu | Lys | Glu | Lys | Asn | Glu | Lys | Glu |
| | | 130 | | | | | 135 | | | | | 140 | | | |
| Arg | Gln | Asp | Phe | Val | Ala | Glu | Lys | Leu | Asp | Gln | Gln | Phe | Arg | Glu | Arg |
| 145 | | | | | 150 | | | | | 155 | | | | | 160 |
| Cys | Glu | Glu | Leu | Arg | Val | Glu | Leu | Leu | Ser | Ile | His | Gln | Lys | Lys | Val |
| | | | | 165 | | | | | 170 | | | | | 175 | |
| Cys | Glu | Glu | Arg | Lys | Ala | Gln | Ile | Ala | Phe | Asn | Glu | Glu | Leu | Ser | Arg |
| | | | 180 | | | | | 185 | | | | | 190 | | |
| Gln | Lys | Leu | Val | Glu | Glu | Gln | Met | Phe | Ser | Lys | Leu | Trp | Glu | Glu | Asp |
| | | | | 195 | | | | | 200 | | | | | 205 | |
| Arg | Leu | Ala | Lys | Glu | Lys | Arg | Glu | Ala | Gln | Glu | Ala | Arg | Arg | Gln | Lys |
| | | 210 | | | | | 215 | | | | | 220 | | | |
| Glu | Leu | Met | Glu | Asn | Thr | Arg | Leu | Gly | Leu | Asn | Ala | Gln | Ile | Thr | Ser |
| 225 | | | | | 230 | | | | | 235 | | | | | 240 |
| Ile | Lys | Ala | Gln | Arg | Gln | Ala | Thr | Gln | Leu | Leu | Lys | Glu | Glu | Glu | Ala |
| | | | | 245 | | | | | 250 | | | | | 255 | |
| Arg | Leu | Val | Glu | Ser | Asn | Asn | Ala | Gln | Ile | Lys | His | Glu | Asn | Glu | Gln |
| | | | 260 | | | | | 265 | | | | | 270 | | |
| Asp | Met | Leu | Lys | Lys | Gln | Lys | Ala | Lys | Gln | Glu | Thr | Arg | Thr | Ile | Leu |
| | | | | 275 | | | | | 280 | | | | | 285 | |
| Gln | Lys | Ala | Leu | Gln | Glu | Arg | Ile | Glu | His | Ile | Gln | Gln | Glu | Tyr | Arg |
| | | 290 | | | | | 295 | | | | | 300 | | | |
| Asp | Glu | Gln | Asp | Leu | Asn | Met | Lys | Leu | Val | Gln | Arg | Ala | Leu | Gln | Asp |

```
305             310              315                320
Leu Gln Glu Glu Ala Asp Lys Lys Gln Lys Arg Glu Asp Met Ile
                325              330                335
Arg Glu Gln Lys Ile Tyr His Lys Tyr Leu Ala Gln Arg Arg Glu Glu
                340              345                350
Glu Lys Ala Gln Glu Lys Glu Phe Asp Arg Ile Leu Glu Glu Asp Lys
                355              360                365
Ala Lys Lys Leu Ala Glu Lys Asp Lys Glu Leu Arg Leu Glu Lys Glu
    370              375              380
Ala Arg Arg Gln Leu Val Asp Glu Val Met Cys Thr Arg Lys Leu Gln
385              390              395                400
Val Gln Glu Lys Leu Gln Arg Glu Ala Lys Glu Gln Glu Glu Arg Ala
                405              410                415
Met Glu Gln Lys His Ile Asn Glu Ser Leu Lys Glu Leu Asn Cys Glu
                420              425                430
Glu Lys Glu Asn Phe Ala Arg Arg Gln Arg Leu Ala Gln Glu Tyr Arg
                435              440              445
Lys Gln Leu Gln Met Gln Ile Ala Tyr Gln Gln Ser Gln Glu Ala
                450              455              460
Glu Lys Glu Glu Lys Arg Arg Glu Phe Glu Ala Gly Val Ala Ala Asn
465              470              475                480
Lys Met Cys Leu Asp Lys Val Gln Glu Val Leu Ser Thr His Gln Val
                485              490                495
Leu Pro Gln Asn Ile His Pro Met Arg Lys Ala Cys Pro Ser Lys Leu
                500              505                510
Pro Pro (2) INFORMATION FOR SEQ ID NO:15:

(i) SEQUENCE CHARACTERISTICS:
        (A) LENGTH: 2555 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

AACGGGAAAT GCTCTGTATC CAAATGCCAG CTGAGATCAT TAGCCACGCT GAAATTCGTT          60

GACTCGTACT GTGCTAAGGT TGCTGCTAGA CGTTGTTAAC AGAGTTAGTG GTCTTTGGTT         120

ATGGTGGTTA GCAGCCCCAC TTATCTGTTC CATACTACCA GTGAATAGTT TAAAATTCAT         180

GTTGCACCTA TAATTTATCC CACATAAATA ATTCAGGCTA TTTATTTTGG CATTCAATTG         240

ATTTTTTTCT CACTTTAAAA AACTGAGGTA TGGAGACTGG TGCTAGCAAC ACGGGATTGG         300

CTAACGCATC CTCTTGCTGT TCCCGGTGTT TGGGCCTTGC CTGTGACAGT GGGAAAAAAA         360

ATGGCCTTGC TGTGCTACAA CCGGAGCTGC GGTCAGCGCT TCGATCCTGA GACCAATTCC         420

GACGATGCTT GCACATATCA CCCAGGCGTT CCAGTCTTTC ACGATGCATT AAAGGGTTGG         480

TCTTGCTGTA AGAGAAGAAC AACTGATTTT TCTGATTTCT TAAGCATTGT AGGCTGTACA         540

AAAGGTAGAC ATAATAGTGA GAAGCCACCT GAGCCAGTCA AACCTGAGGT CAAGACTACT         600

GAGAAGAAGG AACTATCTGA ATTAAAACCA AAATTTCAGG AACACATTCA AGCCCCTAAG         660

ACAGTAGACG CGATAAAAAG ACCAAGCCCA GATGAACCAA TGACAAATTT GGAATTAAAA         720

ATATCTGCYT CCCTTAAAAC AAGCACTTGA TAAACTTAAA CTGTCATCAG GGAATGAAGA         780

AAATAAGAAA AGAAGACAAT GATGAAATTA AGATTGGGAC CTCATGTAAG AATGGAGGGT         840
```

```
GTTCAAAGAC ATATCGGGGT CTAGAGAGTC TAGAAGAAGT CTGTGTATAT CATTCTGGAG      900

TACCTATTTT CCATGAGGGG ACGAAATACT GGAGCTGTTG TAGAAGAAAA ACTTCTGATT      960

TTAATACATT CTTAGACCAA GAGGGCTGTA CAAAAGAGAA ACATGTGGAC TAAAAAAGAT     1020

GCTGGGAAAA AAGTTGTTCC ATGTAGACAT GACTGGCATC AGACTGGAGG TGAAGTTACC     1080

ATTTCAGTAT ATGCTAAAAA CTCACTTCCA GAACTTAGCC GAGTAGAAGC AAATAGCACA     1140

TTGTTAAATG TGCATATTGT ATTTGAAGGA GAGAAGGAAT TTGATCAAAA TGTGAAATTA     1200

TGGGGTGTGA TTGATGTAAA GCGAAGTTAT GTAACTATGA CTGCAACAAA GATTGAAATC     1260

ACTATGAGAA AAGCTGAACC GATGCAGTGG GCAAGCCTTG AACTGCCTGC AGCTAAAAAG     1320

CAGGAAAAAC AAAAAGACGA CACAGCAGAT TGAGTGGGAG ATGGGAGGAA GGCTATTACG     1380

TATTTCAGAA TTTTTAATAC TGTGTGAAGT GGTGGCTTGC TGCTGTCATC TTTTGTTTTG     1440

TTGTTGTGTT ACTGAATGTG GCATTTCAGG GTTAACATTA GGTTCTTAAA AGCCAAAGTC     1500

AGTTTATCTT TTTGTGCCTC TCATCTTTCT TTCGTGTTAT GTAAGATTGA TTATTCGTTT     1560

CTCCCTACTG GTAGGAACCA TAGTTGTGTC CTGTACTTGA AGAGGCTGAA AAATAGCCCA     1620

TAACCATAAT TGCAGTATTT CTTTGTATTT CTCTGTTAAG CAAAGAAATA TTAAGGAACT     1680

TTTTTTATGT CTTTGTATTA TTCCATAATT AGTAAAGCTA ATTGTGAATG TCCAATTTTA     1740

ATGAAATGTC CAATTTTAAT CAGTTTTTTT CATGGATTTG TGTTCTTACG GTACTTGAAA     1800

ATATTTAAGG AAGAGATGAA GCTCTGCAGT TTTTTCTATG TGGGATGATT GCTTTTTTAA     1860

GGAGGATTAA TTCTGAGGTA GTATAGTAAG TAAAGGGGAA TATATGAATT GTTAACAAAT     1920

TAGGATTTGT TTACAACTAC TTGAATTTTT AAATTATGTC AAAACTTACA TTACTTGCCA     1980

AGCAGTATGA TGTAAGAGTA TAGGAAACAT AAATAAGAAT ACAGAGGTAT CAATTTGATT     2040

AAAATTCACC ATTTTATAAG ACTAAGCAAT AATCTTAAAA ACCTCTTTCC TGAATATTTA     2100

AATGTGTTTG TATGGTGTTA TGACTAATTG TTACTGATTT ACAGACTAAG CCCTCTTAAA     2160

ACCTTTAGTT AAATATAAAA AGAAATTATA TATATYTKGC CTCCCTGATG GAAAACTATG     2220

TAAAATTGTA GACTTAAAAG GTTTGTGGAG GCCGGGCGCG GTGGYTCATG CCTGTAATCC     2280

CAGCACTTTG GGAGGCCGAG GCGGGCAGAT CACGAGGTCA GGAGATSGAG ACCATCCTGG     2340

CTAACACGGT GAAACCCCGT CTYTACTAGA AATACAAAAA TTAGCTGGGC GTAGTGGTGG     2400

GTGCCTGTAG TCCCAGCTAC TCAGGAGGCT GAGGCAGGAG AATGGCGTGA ACCTAAGAGG     2460

CGGAGCTGGC AGTGAGCTGA GATTGCGCCA CTGCACTCCA GCCTGGGCGA CAGAGCCAGA     2520

CTCCGACTCA AAAAAAAAAA AAAAAAAAA AAAA                                 2555
```

(2) INFORMATION FOR SEQ ID NO:16:

(i) SEQUENCE CHARACTERISTICS:
        (A) LENGTH: 116 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Met Trp Thr Lys Lys Asp Ala Gly Lys Lys Val Pro Cys Arg His
1               5                   10                  15

Asp Trp His Gln Thr Gly Gly Glu Val Thr Ile Ser Val Tyr Ala Lys
                20                  25                  30

Asn Ser Leu Pro Glu Leu Ser Arg Val Glu Ala Asn Ser Thr Leu Leu
            35                  40                  45
```

```
Asn Val His Ile Val Phe Glu Gly Glu Lys Glu Phe Asp Gln Asn Val
    50                  55                  60

Lys Leu Trp Gly Val Ile Asp Val Lys Arg Ser Tyr Val Thr Met Thr
65                  70                  75                  80

Ala Thr Lys Ile Glu Ile Thr Met Arg Lys Ala Glu Pro Met Gln Trp
                85                  90                  95

Ala Ser Leu Glu Leu Pro Ala Ala Lys Lys Gln Glu Lys Gln Lys Asp
                100                 105                 110

Asp Thr Ala Asp
        115
```

(2) INFORMATION FOR SEQ ID NO:17:

(i) SEQUENCE CHARACTERISTICS:
        (A) LENGTH: 1307 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

```
AGTGTGGACG GCCCACTGGG TTGGTGGTGG TGGGTGCCCG TCACAGGGCT GGAGGTGTGG      60
CCGGCCCACT GGGTTGTGCT TTCTGCCGTA CGTCCCTTCC CATGAGGATG AGATGACCCA     120
TCTGTTGCAT CCCGGCTGCT GATAAAACAA GACCCTCGGA GCCAAGAAAC AACACTGAGT     180
TCCAGATTTC GGAAGGTTCA CGAGTGTTGC CGACACGCCC TCCCAACTGC AGACATCCTC     240
CCTGGAGGAC CTGCTGTGCT CACATGCCCC CCTGTCCAGC GAGGACGACA CCTCCCCGGG     300
CTGTGCAGCC CCCTCCCAGG CACCCTTCAA GGCCTTCCTC AGTCCCCCAG AGCCACATAG     360
CCACCGAGGC ACCGACAGGA AGCTGTCCCC GCTCCTGAGC CCCTTGCAAG ACTCACTGGT     420
GGACAAGACC CTGCTGGAGC CCAGGGAGAT GGTCCGGCCT AAGAAGGTGT GTTTCTCGGA     480
GAGCAGCCTG CCCACCGGGG ACAGGACCAG GAGGAGCTAC TACCTCAATG AGATCCAGAG     540
CTTCGCGGGC GCCGAGAAGG ACGCGCGCGT GGTGGGCGAG ATCGCCTTCC AGCTGGACCG     600
CCGCATCCTG GCCTACGTGT TCCCGGGCGT GACGCGGCTC TACGGCTTCA CGGTGGCCAA     660
CATCCCCGAG AAGATCGAGC AGACCTCCAC CAAGTCTCTG GACGGCTCCG TGGACGAGAG     720
GAAGCTGCGC GAGCTGACGC AGCGCTACCT GGCCCTGAGC GCGCGCCTGG AGAAGCTGGG     780
CTACAGCCGC GACGTGCACC CGGCGTTCAG CGAGTTCCTC ATCAACACCT ACGGAATCCT     840
GAAGCAGCGG CCCGACCTGC GCGCCAACCC CCTGCACAGC AGCCCGGCCG CGCTGCGCAA     900
GCTGGTCATC GACGTGGTGC CCCCCAAGTT CCTGGGCGAC TCGCTGCTGC TGCTCAACTG     960
CCTGTGCGAG CTCTCCAAGG AGGACGGCAA GCCCCTCTTC GCCTGGTGAG CCGCCCCGCG    1020
CCCGCCGCCT TGCCTGCAGT AAACGCGTTT GTTCCAACCC GGGGCCGCGG TGCCTCCTGC    1080
GCGTCCCCCC GGAGGGGAAA GGGCCGCGTC CCCCGCGCGC GAGGCCAGAG AAGGCCCCGC    1140
TCCCACCGGT GCTGGGCCCC GACCGCAGCC CGCCGCTGCC CGCACCTGCG GAGTGCTTCT    1200
CACCCCTCAT TAAAATCATC CGTTTGCAAA AAAAAAAAAA AAAAAAAAAA AAAAAAAAAA    1260
AAAAAAAAAA AAAAAAAAAA AAAAAAAAAA AAAAAAAAAA AAAAAA                   1307
```

(2) INFORMATION FOR SEQ ID NO:18:

(i) SEQUENCE CHARACTERISTICS:
        (A) LENGTH: 186 amino acids
        (B) TYPE: amino acid
        (C) STRANDEDNESS:

(D) TOPOLOGY: linear (ii) MOLECULE TYPE: protein (xi) SEQUENCE DESCRIPTION: SEQ ID NO:18:

```
Met Val Arg Pro Lys Lys Val Cys Phe Ser Glu Ser Ser Leu Pro Thr
1               5                   10                  15

Gly Asp Arg Thr Arg Arg Ser Tyr Tyr Leu Asn Glu Ile Gln Ser Phe
                20                  25                  30

Ala Gly Ala Glu Lys Asp Ala Arg Val Val Gly Glu Ile Ala Phe Gln
            35                  40                  45

Leu Asp Arg Arg Ile Leu Ala Tyr Val Phe Pro Gly Val Thr Arg Leu
50                      55                  60

Tyr Gly Phe Thr Val Ala Asn Ile Pro Glu Lys Ile Glu Gln Thr Ser
65                      70                  75                  80

Thr Lys Ser Leu Asp Gly Ser Val Asp Glu Arg Lys Leu Arg Glu Leu
                85                  90                  95

Thr Gln Arg Tyr Leu Ala Leu Ser Ala Arg Leu Glu Lys Leu Gly Tyr
                100                 105                 110

Ser Arg Asp Val His Pro Ala Phe Ser Glu Phe Leu Ile Asn Thr Tyr
                115                 120                 125

Gly Ile Leu Lys Gln Arg Pro Asp Leu Arg Ala Asn Pro Leu His Ser
130                     135                 140

Ser Pro Ala Ala Leu Arg Lys Leu Val Ile Asp Val Val Pro Pro Lys
145                     150                 155                 160

Phe Leu Gly Asp Ser Leu Leu Leu Leu Asn Cys Leu Cys Glu Leu Ser
                165                 170                 175

Lys Glu Asp Gly Lys Pro Leu Phe Ala Trp
                180                 185
```

(2) INFORMATION FOR SEQ ID NO:19:

(i) SEQUENCE CHARACTERISTICS:
        (A) LENGTH: 3319 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

```
CCGGAAGCTG GAGGAAAACG AAGAGAAGAA GCAGTACCGG GAATCTTACA TCAGTGACAA      60

CCTGGACCTC GACATGGACC AGCTGGAAAA ACGGTCGCGG GCCAGCGGGA GCAGTGCGGG     120

CAGCATGAAA CACAAGCGCC TGTCCCGTCA TTCCACCGCC AGCCACAGCA GTTCCCACAC     180

CTCGGGCATT GAGGCAGACA CCAAGCCCCG GGACACGGGG CCGGAAGACA GCTACTCCAG     240

CAGTGCCATC CACCGCAAGC TGAAAACCTG CAGCTCAATG ACCAGTCATG GCAGCTCCCA     300

CACCTCAGGG GTGGAGAGTG GCGGCAAAGA CCGGCTGGAA GAGGACTTAC AGGACGATGA     360

AATAGAGATG TTGGTTGATG ACCCCCGGGA TCTGGAGCAG ATGAATGAAG AGTCTCTGGA     420

AGTCAGCCCA GACATGTGCA TCTACATCAC AGAGGACATG CTCATGTCGC GGAAGCTGAA     480

TGGACACTCT GGGTTGATTG TGAAAGAAAT TGGGTCTTCC ACCTCGAGCT CTTCAGAAAC     540

AGTTGTTAAG CTTCGTGGCC AGAGTACTGA TTCTCTTCCA CAGACTATAT GTCGGAAACC     600

AAAGACCTCC ACTGATCGAC ACAGCTTGAG CCTCGATGAC ATCAGACTTT ACCAGAAAGA     660

CTTCCTGCGC ATTGCAGGTC TGTGTCAGGA CACTGCTCAG AGTTACACCT TTGGATGTGG     720

CCATGAACTG GATGAGGAAG GCCTCTATTG CAACAGTTGC TTGGCCCAGC AGTGCATCAA     780
```

```
CATCCAAGAT GCTTTTCCAG TCAAAAGAAC CAGCAAATAC TTTTCTCTGG ATCTCACTCA      840

TGATGAAGTT CCAGAGTTTG TTGTGTAAAG TCCGTCTGTG TGCAGCTGTA CAGGCAGCTT      900

ACTGTTTGCT AGAGGATGCG AAAGTCATAA GTTCTTTACA TATTACTTGT GCCATATCTT      960

CTTCACCCTA AACATAGCTC TTTCTTTATA ATATTTGTGA TGATGGAAAC AAAAGCCTTG     1020

GAACAATTGC ACTTTAAGTA TTACACAGAA GTAAAAGAAC TACAGAAAAT GTACAGCAAG     1080

ACAAGTGCCC GGAAGTTCAC TGATCCTTCA GAAGGAAATG CGCTTTACTG ATTGCAAAGC     1140

CTTCAGAATA TTGGAGTGTG GTGTGTTTGC TCATCTGATG CTTTTTAGTT CAGTTACATG     1200

TAACATCACA TTTTTTTTAT CACGTGAAAG ATGTTAGATT TGTTTGCTTA TAAATTTTTT     1260

ACCACTCCCA CATAAAATGC TCATAGTTTG GGAGAGGAAA GAGGGAAGAT TCTCTCTTCT     1320

TTTAACAGAG AGATGATTGC TCTGTATACC CATTGCTTCC TCCCTGAGGC TGTCCCAAAG     1380

TGAACACTGA TGGAGTGGTC AAAATCATAA GATTGTAGCA AGCCAAAGAT ACGTATGTGA     1440

CGGAAGCACA TAAGCAATAA GCAGAAAACC AGAAGTGCAT GCTGTGATGC CTGTGACTCC     1500

TTCATCCCGC TCAGTGCCAT GTCCTCTTTT GTGATCTTCC AGAAAGCTCC AGGATTCATT     1560

TGAGTTCCAC ATCCAAGTAA CAGATGAATT ATATTCATGT TGTAATGCAT TTTGTGGAGT     1620

TTACAAAACC AGTGTCTGTT AAAACTTTGG AAAATGTCTT AGAAAACGTT GGTGCTTGGT     1680

GATGCTTTAT TTGTTTAATT ATCAAGAACA AATTATGGCA ATGCTAGTTT CTGCTTAACC     1740

AAAATACTCT GTGTATATAT TATACATATA TAAATACATG GGATTGTGTA TGTCTATATG     1800

TGTTTAAAGC TTACTATGTC TTCATTTTGG CTTCCATGAC TATCTTTTAT ACATGGAATT     1860

CCTTAAGATT GAGAATATGT CACTGAGTGA ATGATACCTG CAGACAGTCA GTTGATATAT     1920

GTAGAGTTCA GAATGACTGT TTTCTCATGT GCCTTTGGCC ATGATTCTCA ACACTGATTG     1980

TATAACAGAA TTTTGGGGGG AGCTTTTAAA AAATAATGAC TGAGTCTCCC ACCAGACCGA     2040

TTACATCATT CTCTTGTGGC GGGACCCAAG TAGAATTGCC TTTTCTTTTA AAGTTCTCCA     2100

GATGGAGCTA ATATGCAACA AAGTTGAAAA CCACTGATCC TGGGGGTGTC TTGTTAATTT     2160

TGAAGTAAAA GTGTACAGAA GACGTAGTGT ATGAGAAAGG GCCATTTTTA AGACAGTTAC     2220

CTGTTGTGCT GCTGTTACAA TATATAATGA AACCAAGTCA GGGGAGTGAA TTTATCAATC     2280

TTTTGATGTA AAGTAAAAAC GTAGTTCACA CTTCAGGAGA GAACTTCATA GCACAATGTC     2340

TTTCTATAAG ATATTTTTAA TGATTTAGTA TTTTACAACA TTTGTTTACC ATATTTTGAT     2400

ATACCATTTT TTTCTATCTG CCCAGTTTTA TTAAAAAAAC TATATATTAT TTTCTAAAGA     2460

AACAATCATA TTTTTATACA AAATTATGTT TTCAGGTAAC GAAATAGATG TAGGGTACAG     2520

TGGAACATAA GCAGTGTTAC CCCTGGCTGG GAGTCAGTAT TATACAACAA ATGGTGAGCT     2580

GGAACATGCC CTGTCTGTGC TGTCCCTCCT GTGCTGGGTC GCGGATATGT AGGCAACATT     2640

GCCTTATCAC GCTAGGTTCA CCTGACACTT TAAAAGGAAA AAAAGTTCCA TAGAGTTCTG     2700

TGGTCACAAA ATTGTTTTGC TTTTATCAAA TACTTTAATA GAACCAAAGT TGCAGATATT     2760

GGAATGTATG GAAGTATCTC AGTCTCTGCA TAAGAGGATT AAAGTATGAA AGGATCATTT     2820

AATGACTGTT TTACTTATAA GTCATTAAGT AATCCACCAT TTCTTATGGA TGATGCTTAA     2880

GCCTGGTGAG GTTTGTACTC TAAGGAGCCC AGATCATAAT GCAGTGCATT TCCTTAGCCC     2940

TTAGAGTTTC TTGCAAACAT TTAAAAAAAA GACATATTTA AGAAAGAAAG ATAAAGAAAA     3000

AACATATTTA ATTACTGTAA ACAGGTACTG CTTTATGTTT ATTTTCTCTC TACTTCAACC     3060

AAAATCAGAT CTTTGAGGTT TTGCTGACAT TGTTGGTGGT TTTGCACATG TTCTTTCTAA     3120

TTGGATTTAT GAATAGTTCT ATGGGTTTTC AAAGATGAAT CATGCTAAGA ACACTTCTGC     3180
```

```
TTTTTGATCC ACTGTTTGCA GCAGAATTAT ATATATGTAT AGGAAAAATC CACTTTGAAT        3240

AATCCATGTT TTGTATTTGG AAATTGTTTT TAAAAATAAA AAGGAAAGGA AATATAAAAA        3300

AAAAAAAAAA AAAAAAAAA                                                    3319
```

(2) INFORMATION FOR SEQ ID NO:20:

(i) SEQUENCE CHARACTERISTICS:
        (A) LENGTH: 264 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
Met Asp Gln Leu Glu Lys Arg Ser Arg Ala Ser Gly Ser Ser Ala Gly
1               5                   10                  15

Ser Met Lys His Lys Arg Leu Ser Arg His Ser Thr Ala Ser His Ser
            20                  25                  30

Ser Ser His Thr Ser Gly Ile Glu Ala Asp Thr Lys Pro Arg Asp Thr
        35                  40                  45

Gly Pro Glu Asp Ser Tyr Ser Ser Ala Ile His Arg Lys Leu Lys
50                  55                  60

Thr Cys Ser Ser Met Thr Ser His Gly Ser Ser His Thr Ser Gly Val
65                  70                  75                  80

Glu Ser Gly Gly Lys Asp Arg Leu Glu Glu Asp Leu Gln Asp Asp Glu
                85                  90                  95

Ile Glu Met Leu Val Asp Asp Pro Arg Asp Leu Glu Gln Met Asn Glu
            100                 105                 110

Glu Ser Leu Glu Val Ser Pro Asp Met Cys Ile Tyr Ile Thr Glu Asp
        115                 120                 125

Met Leu Met Ser Arg Lys Leu Asn Gly His Ser Gly Leu Ile Val Lys
130                 135                 140

Glu Ile Gly Ser Ser Thr Ser Ser Ser Glu Thr Val Val Lys Leu
145                 150                 155                 160

Arg Gly Gln Ser Thr Asp Ser Leu Pro Gln Thr Ile Cys Arg Lys Pro
                165                 170                 175

Lys Thr Ser Thr Asp Arg His Ser Leu Ser Leu Asp Asp Ile Arg Leu
            180                 185                 190

Tyr Gln Lys Asp Phe Leu Arg Ile Ala Gly Leu Cys Gln Asp Thr Ala
        195                 200                 205

Gln Ser Tyr Thr Phe Gly Cys Gly His Glu Leu Asp Glu Gly Leu
210                 215                 220

Tyr Cys Asn Ser Cys Leu Ala Gln Gln Cys Ile Asn Ile Gln Asp Ala
225                 230                 235                 240

Phe Pro Val Lys Arg Thr Ser Lys Tyr Phe Ser Leu Asp Leu Thr His
                245                 250                 255

Asp Glu Val Pro Glu Phe Val Val
            260
```

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:21:

ANATTCAAGAG AGTTGAACTG AATAACCC                                        29

(2) INFORMATION FOR SEQ ID NO:22:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:22:

ANGGCAGAGCC ACATCCTTCA CAACAGAA                                        29

(2) INFORMATION FOR SEQ ID NO:23:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:23:

GNGTCTGAGTG TCTATGTGAG GGCAAGGA                                        29

(2) INFORMATION FOR SEQ ID NO:24:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:24:

TNGGATAAGCC GGCACAGACG AAGGCCAT                                        29

(2) INFORMATION FOR SEQ ID NO:25:

(i) SEQUENCE CHARACTERISTICS:
          (A) LENGTH: 29 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "oligonucleotide"

(xi) SEQUENCE DESCRIPTION: SEQ ID NO:25:

GNAAGGAAGGA GACAAACACA ATCACCCA                                        29

(2) INFORMATION FOR SEQ ID NO:26:

(i) SEQUENCE CHARACTERISTICS:
          (A) LENGTH: 29 base pairs
          (B) TYPE: nucleic acid
          (C) STRANDEDNESS: single
          (D) TOPOLOGY: linear -continued (ii) MOLECULE TYPE: other nucleic acid
    (A) DESCRIPTION: /desc = "oligonucleotide"

(xi) SEQUENCE DESCRIPTION: SEQ ID NO:26:

TNTTTGTTCTA GCAATTCTAC TTCCGGGA                    29

(2) INFORMATION FOR SEQ ID NO:27:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:27:

TNCTTCCTCAC GTCTCTGTGC CAAATATT                    29

(2) INFORMATION FOR SEQ ID NO:28:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:28:

ANCTCCAGTCT GATGCCAGTC ATGTCTAC                    29

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonulceotide"

(xi) SEQUENCE DESCRIPTION: SEQ ID NO:29:

GNCGGCAACAC TCGTGAACCT TCCGAAAT                    29

(2) INFORMATION FOR SEQ ID NO:30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(xi) SEQUENCE DESCRIPTION: SEQ ID NO:30:

GNCTTGGAACA ATTGCACTTT AAGTATTA                    29

SECRETED PROTEINS AND POLYNUCLEOTIDES ENCODING THEM

This application is a continuation-in-part of application Ser. No. 08/815,047, filed Mar. 14, 1997, now abandoned, the contents of which applications are incorporated herein by reference.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:
  (a) a polynucleotide comprising the nucleotide sequence of SEQ ID NO:1;
  (b) a polynucleotide comprising the nucleotide sequence of SEQ ID NO:1 from nucleotide 533 to nucleotide 673;
  (c) a polynucleotide comprising the nucleotide sequence of SEQ ID NO:1 from nucleotide 596 to nucleotide 673;
  (d) a polynucleotide comprising the nucleotide sequence of SEQ ID NO:1 from nucleotide 1 to nucleotide 664;
  (e) a polynucleotide comprising the nucleotide sequence of the full-length protein coding sequence of clone bd379_1 deposited under accession number ATCC 98361;
  (f) a polynucleotide encoding the full-length protein encoded by the cDNA insert of clone bd379_1 deposited under accession number ATCC 98361;
  (g) a polynucleotide comprising the nucleotide sequence of the mature protein coding sequence of clone bd379_1 deposited under accession number ATCC 98361;
  (h) a polynucleotide encoding the mature protein encoded by the cDNA insert of clone bd379_1 deposited under accession number ATCC 98361;
  (i) a polynucleotide encoding a protein comprising the amino acid sequence of SEQ ID NO:2;
  (j) a polynucleotide encoding a protein comprising a fragment of the amino acid sequence of SEQ ID NO:2 having biological activity;
  (k) a polynucleotide which is an allelic variant of a polynucleotide of (a)–(h) above;
  (l) a polynucleotide which encodes a species homologue of the protein of (i) or (j) above; and
  (m) a polynucleotide capable of hybridizing under stringent conditions to any one of the polynucleotides specified in (a)–(j).

Preferably, such polynucleotide comprises the nucleotide sequence of SEQ ID NO:1 from nucleotide 533 to nucleotide 673; the nucleotide sequence of SEQ ID NO:1 from nucleotide 596 to nucleotide 673; the nucleotide sequence of SEQ ID NO:1 from nucleotide 1 to nucleotide 664; the nucleotide sequence of the full-length protein coding sequence of clone bd379_1 deposited under accession number ATCC 98361; or the nucleotide sequence of the mature protein coding sequence of clone bd379_1 deposited under accession number ATCC 98361. In other preferred embodiments, the polynucleotide encodes the full-length or mature protein encoded by the cDNA insert of clone bd379_1 deposited under accession number ATCC 98361. In yet other preferred embodiments, the present invention provides a polynucleotide encoding a protein comprising the amino acid sequence of SEQ ID NO:2 from amino acid 1 to amino acid 44.

Other embodiments provide the gene corresponding to the cDNA sequence of SEQ ID NO:1.

In other embodiments, the present invention provides a composition comprising a protein, wherein said protein comprises an amino acid sequence selected from the group consisting of:
  (a) the amino acid sequence of SEQ ID NO:2;
  (b) the amino acid sequence of SEQ ID NO:2 from amino acid 1 to amino acid 44;
  (c) fragments of the amino acid sequence of SEQ ID NO:2; and
  (d) the amino acid sequence encoded by the cDNA insert of clone bd379_1 deposited under accession number ATCC 98361;
the protein being substantially free from other mammalian proteins. Preferably such protein comprises the amino acid sequence of SEQ ID NO:2 or the amino acid sequence of SEQ ID NO:2 from amino acid 1 to amino acid 44.

In one embodiment, the present invention provides a composition comprising an isolated polynucleotide selected from the group consisting of:
  (a) a polynucleotide comprising the nucleotide sequence of SEQ ID NO:3;
  (b) a polynucleotide comprising the nucleotide sequence of SEQ ID NO:3 from nucleotide 55 to nucleotide 1008;
  (c) a polynucleotide comprising the nucleotide sequence of SEQ ID NO:3 from nucleotide 952 to nucleotide 1008;
  (d) a polynucleotide comprising the nucleotide sequence of SEQ ID NO:3 from nucleotide 403 to nucleotide 981;
  (e) a polynucleotide comprising the nucleotide sequence of the full-length protein coding sequence of clone bp121_2 deposited under accession number ATCC 98361;

(f) a polynucleotide encoding the full-length protein encoded by the cDNA insert of clone bp121_2 deposited under accession number ATCC 98361;

(g) a polynucleotide comprising the nucleotide sequence of the mature protein coding sequence of clone bp121_2 deposited under accession number ATCC 98361;

(h) a polynucleotide encoding the mature protein encoded by the cDNA insert of clone bp121_2 deposited under accession number ATCC 98361;

(i) a polynucleotide encoding a protein comprising the amino acid sequence of SEQ ID NO:4;

(j) a polynucleotide encoding a protein comprising a fragment of the amino acid sequence of SEQ ID NO:4 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:3 from nucleotide 55 to nucleotide 1008; the nucleotide sequence of SEQ ID NO:3 from nucleotide 952 to nucleotide 1008; the nucleotide sequence of SEQ ID NO:3 from nucleotide 403 to nucleotide 981; the nucleotide sequence of the full-length protein coding sequence of clone bp121_2 deposited under accession number ATCC 98361; or the nucleotide sequence of the mature protein coding sequence of clone bp121_2 deposited under accession number ATCC 98361. In other preferred embodiments, the polynucleotide encodes the full-length or mature protein encoded by the cDNA insert of clone bp121_2 deposited under accession number ATCC 98361. In yet other preferred embodiments, the present invention provides a polynucleotide encoding a protein comprising the amino acid sequence of SEQ ID NO:4 from amino acid 119 to amino acid 309.

Other embodiments provide the gene corresponding to the cDNA sequence of SEQ ID NO:3.

In other embodiments, the present invention provides a composition comprising a protein, wherein said protein comprises an amino acid sequence selected from the group consisting of:

(a) the amino acid sequence of SEQ ID NO:4;

(b) the amino acid sequence of SEQ ID NO:4 from amino acid 119 to amino acid 309;

(c) fragments of the amino acid sequence of SEQ ID NO:4; and (d) the amino acid sequence encoded by the cDNA insert of clone bp121_2 deposited under accession number ATCC 98361;

the protein being substantially free from other mammalian proteins. Preferably such protein comprises the amino acid sequence of SEQ ID NO:4 or the amino acid sequence of SEQ ID NO:4 from amino acid 119 to amino acid 309.

In one embodiment, the present invention provides a composition comprising an isolated polynucleotide selected from the group consisting of:

(a) a polynucleotide comprising the nucleotide sequence of SEQ ID NO:5;

(b) a polynucleotide comprising the nucleotide sequence of SEQ ID NO:5 from nucleotide 52 to nucleotide 639;

(c) a polynucleotide comprising the nucleotide sequence of SEQ ID NO:5 from nucleotide 1 to nucleotide 308;

(d) a polynucleotide comprising the nucleotide sequence of the full-length protein coding sequence of clone bp646_10 deposited under accession number ATCC 98361;

(e) a polynucleotide encoding the full-length protein encoded by the cDNA insert of clone bp646_10 deposited under accession number ATCC 98361;

(f) a polynucleotide comprising the nucleotide sequence of the mature protein coding sequence of clone bp646_10 deposited under accession number ATCC 98361;

(g) a polynucleotide encoding the mature protein encoded by the cDNA insert of clone bp646_10 deposited under accession number ATCC 98361;

(h) a polynucleotide encoding a protein comprising the amino acid sequence of SEQ ID NO:6;

(i) a polynucleotide encoding a protein comprising a fragment of the amino acid sequence of SEQ ID NO:6 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:5 from nucleotide 52 to nucleotide 639; the nucleotide sequence of SEQ ID NO:5 from nucleotide 1 to nucleotide 308; the nucleotide sequence of the full-length protein coding sequence of clone bp646_10 deposited under accession number ATCC 98361; or the nucleotide sequence of the mature protein coding sequence of clone bp646_10 deposited under accession number ATCC 98361. In other preferred embodiments, the polynucleotide encodes the full-length or mature protein encoded by the cDNA insert of clone bp646_10 deposited under accession number ATCC 98361. In yet other preferred embodiments, the present invention provides a polynucleotide encoding a protein comprising the amino acid sequence of SEQ ID NO:6 from amino acid 1 to amino acid 86.

Other embodiments provide the gene corresponding to the cDNA sequence of SEQ ID NO:5.

In other embodiments, the present invention provides a composition comprising a protein, wherein said protein comprises an amino acid sequence selected from the group consisting of:

(a) the amino acid sequence of SEQ ID NO:6;

(b) the amino acid sequence of SEQ ID NO:6 from amino acid 1 to amino acid 86;

(c) fragments of the amino acid sequence of SEQ ID NO:6; and (d) the amino acid sequence encoded by the cDNA insert of clone bp646_10 deposited under accession number ATCC 98361;

the protein being substantially free from other mammalian proteins. Preferably such protein comprises the amino acid sequence of SEQ ID NO:6 or the amino acid sequence of SEQ ID NO:6 from amino acid 1 to amino acid 86.

In one embodiment, the present invention provides a composition comprising an isolated polynucleotide selected from the group consisting of:

(a) a polynucleotide comprising the nucleotide sequence of SEQ ID NO:7;

(b) a polynucleotide comprising the nucleotide sequence of SEQ ID NO:7 from nucleotide 134 to nucleotide 1183;

(c) a polynucleotide comprising the nucleotide sequence of SEQ ID NO:7 from nucleotide 191 to nucleotide 1183;

(d) a polynucleotide comprising the nucleotide sequence of SEQ ID NO:7 from nucleotide 1 to nucleotide 763;

(e) a polynucleotide comprising the nucleotide sequence of the full-length protein coding sequence of clone cf50_1 deposited under accession number ATCC 98361;

(f) a polynucleotide encoding the full-length protein encoded by the cDNA insert of clone cf50_1 deposited under accession number ATCC 98361;

(g) a polynucleotide comprising the nucleotide sequence of the mature protein coding sequence of clone cf50_1 deposited under accession number ATCC 98361;

(h) a polynucleotide encoding the mature protein encoded by the cDNA insert of clone cf50_1 deposited under accession number ATCC 98361;

(i) a polynucleotide encoding a protein comprising the amino acid sequence of SEQ ID NO:8;

(j) a polynucleotide encoding a protein comprising a fragment of the amino acid sequence of SEQ ID NO:8 having biological activity;

(k) a polynucleotide which is an allelic variant of a polynucleotide of (a)–(h) above;

(l) a polynucleotide which encodes a species homologue of the protein of (i) or (j) above; and (m) a polynucleotide capable of hybridizing under stringent conditions to any one of the polynucleotides specified in (a)–(j).

Preferably, such polynucleotide comprises the nucleotide sequence of SEQ ID NO:7 from nucleotide 134 to nucleotide 1183; the nucleotide sequence of SEQ ID NO:7 from nucleotide 191 to nucleotide 1183; the nucleotide sequence of SEQ ID NO:7 from nucleotide 1 to nucleotide 763; the nucleotide sequence of the full-length protein coding sequence of clone cf50_1 deposited under accession number ATCC 98361; or the nucleotide sequence of the mature protein coding sequence of clone cf50_1 deposited under accession number ATCC 98361. In other preferred embodiments, the polynucleotide encodes the full-length or mature protein encoded by the cDNA insert of clone cf50_1 deposited under accession number ATCC 98361. In yet other preferred embodiments, the present invention provides a polynucleotide encoding a protein comprising the amino acid sequence of SEQ ID NO:8 from amino acid 1 to amino acid 210.

Other embodiments provide the gene corresponding to the cDNA sequence of SEQ ID NO:7.

In other embodiments, the present invention provides a composition comprising a protein, wherein said protein comprises an amino acid sequence selected from the group consisting of:

(a) the amino acid sequence of SEQ ID NO:8;

(b) the amino acid sequence of SEQ ID NO:8 from amino acid 1 to amino acid 210;

(c) fragments of the amino acid sequence of SEQ ID NO:8; and (d) the amino acid sequence encoded by the cDNA insert of clone cf50_1 deposited under accession number ATCC 98361;

the protein being substantially free from other mammalian proteins. Preferably such protein comprises the amino acid sequence of SEQ ID NO:8 or the amino acid sequence of SEQ ID NO:8 from amino acid 1 to amino acid 210.

In one embodiment, the present invention provides a composition comprising an isolated polynucleotide selected from the group consisting of:

(a) a polynucleotide comprising the nucleotide sequence of SEQ ID NO:9;

(b) a polynucleotide comprising the nucleotide sequence of SEQ ID NO:9 from nucleotide 740 to nucleotide 2245;

(c) a polynucleotide comprising the nucleotide sequence of SEQ ID NO:9 from nucleotide 1 to nucleotide 463;

(d) a polynucleotide comprising the nucleotide sequence of the full-length protein coding sequence of clone cw1543_3 deposited under accession number ATCC 98361;

(e) a polynucleotide encoding the full-length protein encoded by the cDNA insert of clone cw1543_3 deposited under accession number ATCC 98361;

(f) a polynucleotide comprising the nucleotide sequence of the mature protein coding sequence of clone cw1543_3 deposited under accession number ATCC 98361;

(g) a polynucleotide encoding the mature protein encoded by the cDNA insert of clone cw1543_3 deposited under accession number ATCC 98361;

(h) a polynucleotide encoding a protein comprising the amino acid sequence of SEQ ID NO:10;

(i) a polynucleotide encoding a protein comprising a fragment of the amino acid sequence of SEQ ID NO:10 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:9 from nucleotide 740 to nucleotide 2245; the nucleotide sequence of SEQ ID NO:9 from nucleotide 1 to nucleotide 463; the nucleotide sequence of the full-length protein coding sequence of clone cw1543_3 deposited under accession number ATCC 98361; or the nucleotide sequence of the mature protein coding sequence of clone cw1543_3 deposited under accession number ATCC 98361. In other preferred embodiments, the polynucleotide encodes the full-length or mature protein encoded by the cDNA insert of clone cw1543_3 deposited under accession number ATCC 98361.

Other embodiments provide the gene corresponding to the cDNA sequence of SEQ ID NO:9.

In other embodiments, the present invention provides a composition comprising a protein, wherein said protein comprises an amino acid sequence selected from the group consisting of:

(a) the amino acid sequence of SEQ ID NO:10;

(b) fragments of the amino acid sequence of SEQ ID NO:10; and (c) the amino acid sequence encoded by the cDNA insert of clone cw1543_3 deposited under accession number ATCC 98361;

the protein being substantially free from other mammalian proteins. Preferably such protein comprises the amino acid sequence of SEQ ID NO:10.

In one embodiment, the present invention provides a composition comprising an isolated polynucleotide selected from the group consisting of:

(a) a polynucleotide comprising the nucleotide sequence of SEQ ID NO:11;

(b) a polynucleotide comprising the nucleotide sequence of SEQ ID NO:11 from nucleotide 952 to nucleotide 1074;

(c) a polynucleotide comprising the nucleotide sequence of SEQ ID NO:11 from nucleotide 524 to nucleotide 1059;

(d) a polynucleotide comprising the nucleotide sequence of the full-length protein coding sequence of clone da389_1 deposited under accession number ATCC 98361;

(e) a polynucleotide encoding the full-length protein encoded by the cDNA insert of clone da389_1 deposited under accession number ATCC 98361;

(f) a polynucleotide comprising the nucleotide sequence of the mature protein coding sequence of clone da389_1 deposited under accession number ATCC 98361;

(g) a polynucleotide encoding the mature protein encoded by the cDNA insert of clone da389_1 deposited under accession number ATCC 98361;

(h) a polynucleotide encoding a protein comprising the amino acid sequence of SEQ ID NO:12;

(i) a polynucleotide encoding a protein comprising a fragment of the amino acid sequence of SEQ ID NO:12 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:11 from nucleotide 952 to nucleotide 1074; the nucleotide sequence of SEQ ID NO:11 from nucleotide 524 to nucleotide 1059; the nucleotide sequence of the full-length protein coding sequence of clone da389_1 deposited under accession number ATCC 98361; or the nucleotide sequence of the mature protein coding sequence of clone da389_1 deposited under accession number ATCC 98361. In other preferred embodiments, the polynucleotide encodes the full-length or mature protein encoded by the cDNA insert of clone da389_1 deposited under accession number ATCC 98361. In yet other preferred embodiments, the present invention provides a polynucleotide encoding a protein comprising the amino acid sequence of SEQ ID NO:12 from amino acid 1 to amino acid 36.

Other embodiments provide the gene corresponding to the cDNA sequence of SEQ ID NO:11.

In other embodiments, the present invention provides a composition comprising a protein, wherein said protein comprises an amino acid sequence selected from the group consisting of:

(a) the amino acid sequence of SEQ ID NO:12;

(b) the amino acid sequence of SEQ ID NO:12 from amino acid 1 to amino acid 36;

(c) fragments of the amino acid sequence of SEQ ID NO:12; and (d) the amino acid sequence encoded by the cDNA insert of clone da389_1 deposited under accession number ATCC 98361;

the protein being substantially free from other mammalian proteins. Preferably such protein comprises the amino acid sequence of SEQ ID NO:12 or the amino acid sequence of SEQ ID NO:12 from amino acid 1 to amino acid 36.

In one embodiment, the present invention provides a composition comprising an isolated polynucleotide selected from the group consisting of:

(a) a polynucleotide comprising the nucleotide sequence of SEQ ID NO:13;

(b) a polynucleotide comprising the nucleotide sequence of SEQ ID NO:13 from nucleotide 78 to nucleotide 1619;

(c) a polynucleotide comprising the nucleotide sequence of SEQ ID NO:13 from nucleotide 604 to nucleotide 1307;

(d) a polynucleotide comprising the nucleotide sequence of the full-length protein coding sequence of clone dd71_2 deposited under accession number ATCC 98361;

(e) a polynucleotide encoding the full-length protein encoded by the cDNA insert of clone dd71_2 deposited under accession number ATCC 98361;

(f) a polynucleotide comprising the nucleotide sequence of the mature protein coding sequence of clone dd71_2 deposited under accession number ATCC 98361;

(g) a polynucleotide encoding the mature protein encoded by the cDNA insert of clone dd71_2 deposited under accession number ATCC 98361;

(h) a polynucleotide encoding a protein comprising the amino acid sequence of SEQ ID NO:14;

(i) a polynucleotide encoding a protein comprising a fragment of the amino acid sequence of SEQ ID NO:14 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:13 from nucleotide 78 to nucleotide 1619; the nucleotide sequence of SEQ ID NO:13 from nucleotide 604 to nucleotide 1307; the nucleotide sequence of the full-length protein coding sequence of clone dd71_2 deposited under accession number ATCC 98361; or the nucleotide sequence of the mature protein coding sequence of clone dd71_2 deposited under accession number ATCC 98361. In other preferred embodiments, the polynucleotide encodes the full-length or mature protein encoded by the cDNA insert of clone dd71_2 deposited under accession number ATCC 98361. In yet other preferred embodiments, the present invention provides a polynucleotide encoding a protein comprising the amino acid sequence of SEQ ID NO:14 from amino acid 200 to amino acid 410.

Other embodiments provide the gene corresponding to the cDNA sequence of SEQ ID NO:13.

In other embodiments, the present invention provides a composition comprising a protein, wherein said protein comprises an amino acid sequence selected from the group consisting of:

(a) the amino acid sequence of SEQ ID NO:14;

(b) the amino acid sequence of SEQ ID NO:14 from amino acid 200 to amino acid 410;

(c) fragments of the amino acid sequence of SEQ ID NO:14; and (d) the amino acid sequence encoded by the cDNA insert of clone dd71_2 deposited under accession number ATCC 98361;

the protein being substantially free from other mammalian proteins. Preferably such protein comprises the amino acid sequence of SEQ ID NO:14 or the amino acid sequence of SEQ ID NO:14 from amino acid 200 to amino acid 410.

In one embodiment, the present invention provides a composition comprising an isolated polynucleotide selected from the group consisting of:
 (a) a polynucleotide comprising the nucleotide sequence of SEQ ID NO:15;
 (b) a polynucleotide comprising the nucleotide sequence of SEQ ID NO:15 from nucleotide 1003 to nucleotide 1350;
 (c) a polynucleotide comprising the nucleotide sequence of SEQ ID NO:15 from nucleotide 714 to nucleotide 1320;
 (d) a polynucleotide comprising the nucleotide sequence of the full-length protein coding sequence of clone dm221_1 deposited under accession number ATCC 98361;
 (e) a polynucleotide encoding the full-length protein encoded by the cDNA insert of clone dm221_1 deposited under accession number ATCC 98361;
 (f) a polynucleotide comprising the nucleotide sequence of the mature protein coding sequence of clone dm221_1 deposited under accession number ATCC 98361;
 (g) a polynucleotide encoding the mature protein encoded by the cDNA insert of clone dm221_1 deposited under accession number ATCC 98361;
 (h) a polynucleotide encoding a protein comprising the amino acid sequence of SEQ ID NO:16;
 (i) a polynucleotide encoding a protein comprising a fragment of the amino acid sequence of SEQ ID NO:16 having biological activity;
 (j) a polynucleotide which is an allelic variant of a polynucleotide of (a)–(g) above;
 (k) a polynucleotide which encodes a species homologue of the protein of (h) or (i) above; and
 (l) a polynucleotide capable of hybridizing under stringent conditions to any one of the polynucleotides specified in (a)–(i).

Preferably, such polynucleotide comprises the nucleotide sequence of SEQ ID NO:15 from nucleotide 1003 to nucleotide 1350; the nucleotide sequence of SEQ ID NO:15 from nucleotide 714 to nucleotide 1320; the nucleotide sequence of the full-length protein coding sequence of clone dm221_1 deposited under accession number ATCC 98361; or the nucleotide sequence of the mature protein coding sequence of clone dm221_1 deposited under accession number ATCC 98361. In other preferred embodiments, the polynucleotide encodes the full-length or mature protein encoded by the cDNA insert of clone dm221_1 deposited under accession number ATCC 98361. In yet other preferred embodiments, the present invention provides a polynucleotide encoding a protein comprising the amino acid sequence of SEQ ID NO:16 from amino acid 1 to amino acid 106.

Other embodiments provide the gene corresponding to the cDNA sequence of SEQ ID NO:15.

In other embodiments, the present invention provides a composition comprising a protein, wherein said protein comprises an amino acid sequence selected from the group consisting of:
 (a) the amino acid sequence of SEQ ID NO:16;
 (b) the amino acid sequence of SEQ ID NO:16 from amino acid 1 to amino acid 106;
 (c) fragments of the amino acid sequence of SEQ ID NO:16; and
 (d) the amino acid sequence encoded by the cDNA insert of clone dm221_1 deposited under accession number ATCC 98361;

the protein being substantially free from other mammalian proteins. Preferably such protein comprises the amino acid sequence of SEQ ID NO:16 or the amino acid sequence of SEQ ID NO:16 from amino acid 1 to amino acid 106.

In one embodiment, the present invention provides a composition comprising an isolated polynucleotide selected from the group consisting of:
 (a) a polynucleotide comprising the nucleotide sequence of SEQ ID NO:17;
 (b) a polynucleotide comprising the nucleotide sequence of SEQ ID NO:17 from nucleotide 449 to nucleotide 1006;
 (c) a polynucleotide comprising the nucleotide sequence of SEQ ID NO:17 from nucleotide 1 to nucleotide 331;
 (d) a polynucleotide comprising the nucleotide sequence of the full-length protein coding sequence of clone dx279_1 deposited under accession number ATCC 98361;
 (e) a polynucleotide encoding the full-length protein encoded by the cDNA insert of clone dx279_1 deposited under accession number ATCC 98361;
 (f) a polynucleotide comprising the nucleotide sequence of the mature protein coding sequence of clone dx279_1 deposited under accession number ATCC 98361;
 (g) a polynucleotide encoding the mature protein encoded by the cDNA insert of clone dx279_1 deposited under accession number ATCC 98361;
 (h) a polynucleotide encoding a protein comprising the amino acid sequence of SEQ ID NO:18;
 (i) a polynucleotide encoding a protein comprising a fragment of the amino acid sequence of SEQ ID NO:18 having biological activity;
 (j) a polynucleotide which is an allelic variant of a polynucleotide of (a)–(g) above;
 (k) a polynucleotide which encodes a species homologue of the protein of (h) or (i) above; and
 (l) a polynucleotide capable of hybridizing under stringent conditions to any one of the polynucleotides specified in (a)–(i).

Preferably, such polynucleotide comprises the nucleotide sequence of SEQ ID NO:17 from nucleotide 449 to nucleotide 1006; the nucleotide sequence of SEQ ID NO:17 from nucleotide 1 to nucleotide 331; the nucleotide sequence of the full-length protein coding sequence of clone dx279_1 deposited under accession number ATCC 98361; or the nucleotide sequence of the mature protein coding sequence of clone dx279_1 deposited under accession number ATCC 98361. In other preferred embodiments, the polynucleotide encodes the full-length or mature protein encoded by the cDNA insert of clone dx279_1 deposited under accession number ATCC 98361.

Other embodiments provide the gene corresponding to the cDNA sequence of SEQ ID NO:17.

In other embodiments, the present invention provides a composition comprising a protein, wherein said protein comprises an amino acid sequence selected from the group consisting of:

(a) the amino acid sequence of SEQ ID NO:18;

(b) fragments of the amino acid sequence of SEQ ID NO:18; and (c) the amino acid sequence encoded by the cDNA insert of clone dx279_1 deposited under accession number ATCC 98361;

the protein being substantially free from other mammalian proteins. Preferably such protein comprises the amino acid sequence of SEQ ID NO:18.

In one embodiment, the present invention provides a composition comprising an isolated polynucleotide selected from the group consisting of:

(a) a polynucleotide comprising the nucleotide sequence of SEQ ID NO:19;

(b) a polynucleotide comprising the nucleotide sequence of SEQ ID NO:19 from nucleotide 74 to nucleotide 865;

(c) a polynucleotide comprising the nucleotide sequence of SEQ ID NO:19 from nucleotide 538 to nucleotide 1044;

(d) a polynucleotide comprising the nucleotide sequence of the full-length protein coding sequence of clone gm243_1 deposited under accession number ATCC 98361;

(e) a polynucleotide encoding the full-length protein encoded by the cDNA insert of clone gm243_1 deposited under accession number ATCC 98361;

(f) a polynucleotide comprising the nucleotide sequence of the mature protein coding sequence of clone gm243_1 deposited under accession number ATCC 98361;

(g) a polynucleotide encoding the mature protein encoded by the cDNA insert of clone gm243_1 deposited under accession number ATCC 98361;

(h) a polynucleotide encoding a protein comprising the amino acid sequence of SEQ ID NO:20;

(i) a polynucleotide encoding a protein comprising a fragment of the amino acid sequence of SEQ ID NO:20 having biological activity;

(j) a polynucleotide which is an allelic variant of a polynucleotide of (a)–(g) above;

(k) a polynucleotide which encodes a species homologue of the protein of (h) or (i) above; and (l) a polynucleotide capable of hybridizing under stringent conditions to any one of the polynucleotides specified in (a)–(i).

Preferably, such polynucleotide comprises the nucleotide sequence of SEQ ID NO:19 from nucleotide 74 to nucleotide 865; the nucleotide sequence of SEQ ID NO:19 from nucleotide 538 to nucleotide 1044; the nucleotide sequence of the full-length protein coding sequence of clone gm243_1 deposited under accession number ATCC 98361; or the nucleotide sequence of the mature protein coding sequence of clone gm243_1 deposited under accession number ATCC 98361. In other preferred embodiments, the polynucleotide encodes the full-length or mature protein encoded by the cDNA insert of clone gm243_1 deposited under accession number ATCC 98361.

Other embodiments provide the gene corresponding to the cDNA sequence of SEQ ID NO:19.

In other embodiments, the present invention provides a composition comprising a protein, wherein said protein comprises an amino acid sequence selected from the group consisting of:

(a) the amino acid sequence of SEQ ID NO:20;

(b) fragments of the amino acid sequence of SEQ ID NO:20; and (c) the amino acid sequence encoded by the cDNA insert of clone gm243_1 deposited under accession number ATCC 98361;

the protein being substantially free from other mammalian proteins. Preferably such protein comprises the amino acid sequence of SEQ ID NO:20.

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing a protein, which comprise:

(a) growing a culture of the host cell transformed with such polynucleotide compositions in a suitable culture medium; and (b) purifying the protein from the culture.

The protein produced according to such methods is also provided by the present invention. Preferred embodiments include those in which the protein produced by such process is a mature form of the protein.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

DETAILED DESCRIPTION

Isolated Proteins and Polynucleotides

Figure 1A:
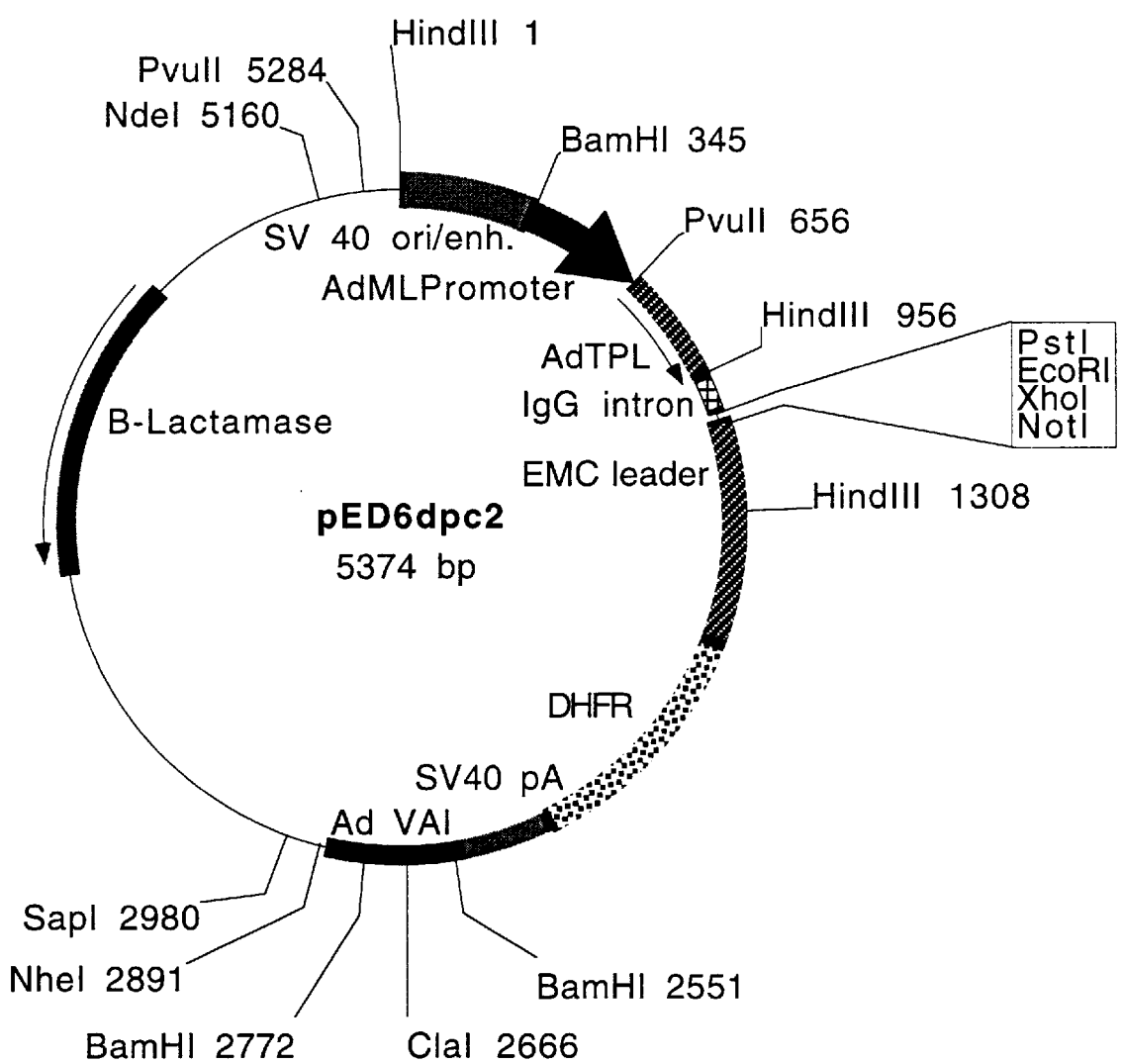
FIGS. 1A and 1B is a schematic representation of the pED6 and pNOTs vectors used for deposit of clones disclosed herein.

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "bd379_1"

A polynucleotide of the present invention has been identified as clone "bd379_1". bd379_1 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. bd379_1 is a full-length clone, including the entire coding sequence of a secreted protein (also referred to herein as "bd379_1 protein").

The nucleotide sequence of bd379_1 as presently determined is reported in SEQ ID NO:1. What applicants presently believe to be the proper reading frame and the predicted amino acid sequence of the bd379_1 protein corresponding to the foregoing nucleotide sequence is reported in SEQ ID NO:2. Amino acids 9 to 21 are a predicted leader/signal sequence, with the predicted mature amino acid sequence beginning at amino acid 22, or are a transmembrane domain.

The EcoRI/NotI restriction fragment obtainable from the deposit containing clone bd379_1 should be approximately 1200 bp.

The nucleotide sequence disclosed herein for bd379_1 was searched against the GenBank and GeneSeq nucleotide sequence databases using BLASTN/BLASTX and FASTA search protocols. bd379_1 demonstrated at least some similarity with sequences identified as F05256 (*H. sapiens* partial cDNA sequence; clone c-05b06), R60369 (yh04b03.r1 *Homo sapiens* cDNA clone 42053 5'), and W39550 (zc18g02.r1 Soares parathyroid tumor NbHPA *Homo sapiens* cDNA clone 322706 5'). Based upon sequence similarity, bd379_1 proteins and each similar protein or peptide may share at least some activity.

Clone "bp121_2"

A polynucleotide of the present invention has been identified as clone "bp121_2". bp121_2 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. bp121_2 is a full-length clone, including the entire coding sequence of a secreted protein (also referred to herein as "bp121_2 protein").

The nucleotide sequence of bp121_2 as presently determined is reported in SEQ ID NO:3. What applicants presently believe to be the proper reading frame and the predicted amino acid sequence of the bp121_2 protein corresponding to the foregoing nucleotide sequence is reported in SEQ ID NO:4. Amino acids 287 to 299 are a predicted leader/signal sequence, with the predicted mature amino acid sequence beginning at amino acid 300, or are a transmembrane domain.

The EcoRI/NotI restriction fragment obtainable from the deposit containing clone bp121_2 should be approximately 4175 bp.

The nucleotide sequence disclosed herein for bp121_2 was searched against the GenBank and GeneSeq nucleotide sequence databases using BLASTN/BLASTX and FASTA search protocols. bp121_2 demonstrated at least some similarity with sequences identified as AA261860 (zs18g12.s1 NCI_CGAP_GCB1 *Homo sapiens* cDNA clone IMAGE:685606 3'), AA478628 (zv19g09.s1 Soares NhHMPu S1 *Homo sapiens* cDNA clone 754144 3' similar to WP D1022.1 CE02575 UBIQUITIN-CONJUGATING ENZYME), H43996 (yo70h10.r1 *Homo sapiens* cDNA clone 183331 5'), N20622 (yx46f08.r1 *Homo sapiens* cDNA clone 264807 5'), N34063 (yx78a05.r1 *Homo sapiens* cDNA clone 267824 5' similar to D82419 similar to none), N57554 (yy81e07.s1 *Homo sapiens* cDNA clone 279972 3'), U23517 (Caenorhabditis elegans cosmid D1022), W19342 (zb90c09.s1 Soares senescent fibroblasts NbHSF *Homo sapiens* cDNA clone 310864 3' similar to WP D1022.1 CE02575 UBIQUITIN-CONJUGATING ENZYME), and W81357 (zd86c08.s1 Soares fetal heart NbHH19W *Homo sapiens* cDNA clone 347534 3' similar to WP D1022.1 CE02575 UBIQUITIN-CONJUGATING ENZYME). The predicted amino acid sequence disclosed herein for bp121_2 was searched against the GenPept and GeneSeq amino acid sequence databases using the BLASTX search protocol. The predicted bp121_2 protein demonstrated at least some similarity to sequences identified as U23517 (similar to ubiquitin conjugating enzyme [Caenorhabditis elegans]) and W05315 (Ubiquitin conjugating enzyme 9). Based upon sequence similarity, bp121_2 proteins and each similar protein or peptide may share at least some activity. The TopPredII computer program predicts a potential transmembrane domain within the bp121_2 protein sequence centered around amino acid 110 of SEQ ID NO:4.

Clone "bp646_10"

A polynucleotide of the present invention has been identified as clone "bp646_10". bp646_10 was isolated from a human fetal kidney cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. bp646_10 is a full-length clone, including the entire coding sequence of a secreted protein (also referred to herein as "bp646_10 protein").

The nucleotide sequence of bp646_10 as presently determined is reported in SEQ ID NO:5. What applicants presently believe to be the proper reading frame and the predicted amino acid sequence of the bp646_10 protein corresponding to the foregoing nucleotide sequence is reported in SEQ ID NO:6.

The EcoRI/NotI restriction fragment obtainable from the deposit containing clone bp646_10 should be approximately 1800 bp.

The nucleotide sequence disclosed herein for bp646_10 was searched against the GenBank and GeneSeq nucleotide sequence databases using BLASTN/BLASTX and FASTA search protocols. bp646_10 demonstrated at least some similarity with sequences identified as AA040456 (zk46f10.r1 Soares pregnant uterus NbHPU *Homo sapiens* cDNA clone 485899 5'), AA101294 (zn71f03.r1 Stratagene NT2 neuronal precursor 937230 *Homo sapiens* cDNA clone 563645 5' similar to WP K07E3.6 CE04722 TRANSLOCATING ATPASE), AA179341 (zp48f01.s1 Stratagene HeLa cell s3 937216 *Homo sapiens* cDNA clone 612697 3'), N54113 (yz02e02.r1 *Homo sapiens* cDNA clone 281882 5'), T21123 (Human gene signature HUMGS02428), U63315 (Rattus norvegicus 25-Dx (25Dx) mRNA, complete cds), X99714 (S. scrofa mRNA for steriod membrane binding protein), and Y12711 (*H. sapiens* mRNA for putative progesterone binding). The predicted amino acid sequence disclosed herein for bp646_10 was searched against the GenPept and GeneSeq amino acid sequence databases using the BLASTX search protocol. The predicted bp646_10 protein demonstrated at least some similarity to sequences identified as U63315 (25-Dx [Rattus norvegicus]), X99714 (steroid membrane binding protein [Sus scrofa]), amd Y12711 (putative progesterone binding protein). Based upon sequence similarity, bp646_10 proteins and each similar protein or peptide may share at least some activity. The TopPredII computer program predicts a potential transmembrane domain within the bp646__10 protein sequence centered around amino acid 40 of SEQ ID NO:6.

Clone "cf50__1"

A polynucleotide of the present invention has been identified as clone "cf50__1". cf50__1 was isolated from a human adult placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. cf50__1 is a full-length clone, including the entire coding sequence of a secreted protein (also referred to herein as "cf50__1 protein").

The nucleotide sequence of cf50__1 as presently determined is reported in SEQ ID NO:7. What applicants presently believe to be the proper reading frame and the predicted amino acid sequence of the cf50__1 protein corresponding to the foregoing nucleotide sequence is reported in SEQ ID NO:8. Amino acids 7 to 19 are a predicted leader/signal sequence, with the predicted mature amino acid sequence beginning at amino acid 20, or are a transmembrane domain.

The EcoRI/NotI restriction fragment obtainable from the deposit containing clone cf50__1 should be approximately 1500 bp.

The nucleotide sequence disclosed herein for cf50__1 was searched against the GenBank and GeneSeq nucleotide sequence databases using BLASTN/BLASTX and FASTA search protocols. cf50__1 demonstrated at least some similarity with sequences identified as H15004 (y126c09.s1 *Homo sapiens* cDNA clone 159376 3'), H52859 (EST0013 *Homo sapiens* cDNA clone HTN-6-19), and R86003 (yp12c03.r1 *Homo sapiens* cDNA clone 187204 5'). Based upon sequence similarity, cf50__1 proteins and each similar protein or peptide may share at least some activity.

Clone "cw1543__3"

A polynucleotide of the present invention has been identified as clone "cw1543__3". cw1543__3 was isolated from a human fetal brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. cw1543__3 is a full-length clone, including the entire coding sequence of a secreted protein (also referred to herein as "cw1543__3 protein").

The nucleotide sequence of cw1543__3 as presently determined is reported in SEQ ID NO:9. What applicants presently believe to be the proper reading frame and the predicted amino acid sequence of the cw1543__3 protein corresponding to the foregoing nucleotide sequence is reported in SEQ ID NO:10.

The EcoRI/NotI restriction fragment obtainable from the deposit containing clone cw1543__3 should be approximately 3300 bp.

The nucleotide sequence disclosed herein for cw1543__3 was searched against the GenBank and GeneSeq nucleotide sequence databases using BLASTN/BLASTX and FASTA search protocols. cw1543__3 demonstrated at least some similarity with sequences identified as AA021431 (ze68f09.s1 Soares retina N2b4HR *Homo sapiens* cDNA clone 364169 3' similar to PIR:A55626 A55626 monocarboxylate transporter MCT2—golden hamster), R68272 (yi06c07.s1 *Homo sapiens* cDNA clone 138444 3'), and U79304 (Human clone 23909 mRNA, partial cds). The predicted amino acid sequence disclosed herein for cw1543__3 was searched against the GenPept and GeneSeq amino acid sequence databases using the BLASTX search protocol. The predicted cw1543__3 protein demonstrated at least some similarity to sequences identified as U62316 (monocarboxylate transporter 2 [Rattus norvegicus]), U79304 (unknown [*Homo sapiens*]), and AF000240 (monocarboxylate transporter 3 [Gallus gallus]). Based upon sequence similarity, cw1543__3 proteins and each similar protein or peptide may share at least some activity.

Clone "da389__1"

A polynucleotide of the present invention has been identified as clone "da389__1". da389__1 was isolated from a human adult placenta cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. da389__1 is a full-length clone, including the entire coding sequence of a secreted protein (also referred to herein as "da389__1 protein").

The nucleotide sequence of da389__1 as presently determined is reported in SEQ ID NO:11. What applicants presently believe to be the proper reading frame and the predicted amino acid sequence of the da389__1 protein corresponding to the foregoing nucleotide sequence is reported in SEQ ID NO:12.

The EcoRI/NotI restriction fragment obtainable from the deposit containing clone da389__1 should be approximately 2000 bp.

The nucleotide sequence disclosed herein for da389__1 was searched against the GenBank and GeneSeq nucleotide sequence databases using BLASTN/BLASTX and FASTA search protocols. da389__1 demonstrated at least some similarity with sequences identified as R46114 (yg49g06.s1 *Homo sapiens* cDNA clone 36151 3' similar to contains L1 repetitive element), R89713 (ym99h07.r1 *Homo sapiens* cDNA clone 167101 5'), Z63670 (*H. sapiens* CpG island DNA genomic MseI fragment, clone 89b11, forward read cpg89b11.ft1a), and Z82170 (Human DNA sequence from PAC 326L13 containing brain-4 mRNA ESTs and polymorphic CA repeat). Based upon sequence similarity, da389__1 proteins and each similar protein or peptide may share at least some activity. The nucleotide sequence of da389__1 indicates that it may contain a repetitive element.

Clone "dd71__2"

A polynucleotide of the present invention has been identified as clone "dd71__2". dd71__2 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. dd71__2 is a full-length clone, including the entire coding sequence of a secreted protein (also referred to herein as "dd71__2 protein").

The nucleotide sequence of dd71__2 as presently determined is reported in SEQ ID NO:13. What applicants presently believe to be proper reading frame and the predicted amino acid sequence of the dd71__2 protein corresponding to the foregoing nucleotide sequence is reported in SEQ ID NO: 14.

The EcoRI/NotI restriction fragment obtainable from the deposit containing clone dd71__2 should be approximately 1700 bp.

The nucleotide sequence disclosed herein for dd71__2 was searched against the GenBank and GeneSeq nucleotide sequence databases using BLASTN/BLASTX and FASTA search protocols. dd71__2 demonstrated at least some similarity with sequences identified as AA011156 (ze34h02.r1 Soares retina N2b4HR *Homo sapiens* cDNA clone 360915 5'), H64206 (EST0047 *Homo sapiens* cDNA clone HTN-6-41), U40719 (Rattus norvegicus S-adenosylmeth), and Z31048 (M. musculus expressed sequence tag MTEST167). The predicted amino acid sequence disclosed herein for dd71_2 was searched against the GenPept and GeneSeq amino acid sequence databases using the BLASTX search protocol. The predicted dd71_2 protein demonstrated at least some similarity to sequences identified as L09190 (trichohyalin [*Homo sapiens*]). Based upon sequence similarity, dd71_2 proteins and each similar protein or peptide may share at least some activity.

Clone "dm221_1"

A polynucleotide of the present invention has been identified as clone "dm221_1". dm221_1 was isolated from a human adult brain cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. dm221_1 is a full-length clone, including the entire coding sequence of a secreted protein (also referred to herein as "dm221_1 protein").

The nucleotide sequence of dm221_1 as presently determined is reported in SEQ ID NO:15. What applicants presently believe to be the proper reading frame and the predicted amino acid sequence of the dm221_1 protein corresponding to the foregoing nucleotide sequence is reported in SEQ ID NO:16.

The EcoRI/NotI restriction fragment obtainable from the deposit containing clone dm221_1 should be approximately 2500 bp.

The nucleotide sequence disclosed herein for dm221_1 was searched against the GenBank and GeneSeq nucleotide sequence databases using BLASTN/BLASTX and FASTA search protocols. dm221_1 demonstrated at least some similarity with sequences identified as AA117998 (mn06h05.r1 Beddington mouse embryonic region Mus musculus cDNA clone 537177 5'), AA164251 (zq46c05.s1 Stratagene hNT neuron (#937233) *Homo sapiens* cDNA clone 632744 3' similar to contains Alu repetitive element), AA333321 (EST37403 Embryo, 8 week I *Homo sapiens* cDNA 5' end), N93607 (zb69g11.s1 Soares fetal lung NbHL19W *Homo sapiens* cDNA clone 308900 3'), U14568 (***ALU WARNING: Human Alu-Sb subfamily consensus sequence), U57007 (Human Ya5 subfamily Alu sequence), W20519 (zb26g03.r1 Soares fetal lung NbHL19W *Homo sapiens* cDNA clone 303220 5'), and W25502 (zb69g11.r1 Soares fetal lung NbHL19W *Homo sapiens* cDNA clone 308900 5'). The predicted amino acid sequence disclosed herein for dm221_1 was searched against the GenPept and GeneSeq amino acid sequence databases using the BLASTX search protocol. The predicted dm221_1 protein demonstrated at least some similarity to sequences identified as S58722 (X-linked retinopathy protein {C-terminal, clone XEH.8c} [human, Peptide Partial, 100 aa] [*Homo sapiens*]). Based upon sequence similarity, dm221_1 proteins and each similar protein or peptide may share at least some activity. The nucleotide sequence of dm221_1 indicates that it may contain an Alu repetitive element.

Clone "dx279_1"

A polynucleotide of the present invention has been identified as clone "dx279_1". dx279_1 was isolated from a human adult testes cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. dx279_1 is a full-length clone, including the entire coding sequence of a secreted protein (also referred to herein as "dx279_1 protein").

The nucleotide sequence of dx279_1 as presently determined is reported in SEQ ID NO:17. What applicants presently believe to be the proper reading frame and the predicted amino acid sequence of the dx279_1 protein corresponding to the foregoing nucleotide sequence is reported in SEQ ID NO:18.

The EcoRI/NotI restriction fragment obtainable from the deposit containing clone dx279_1 should be approximately 1300 bp.

The nucleotide sequence disclosed herein for dx279_1 was searched against the GenBank and GeneSeq nucleotide sequence databases using BLASTN/BLASTX and FASTA search protocols. dx279_1 demonstrated at least some similarity with sequences identified as AA255685 (zs22e05.r1 NCI_CGAP_GCB1 *Homo sapiens* cDNA clone 685952 5'), R46317 (yj53g03.r1 *Homo sapiens* cDNA clone 152500 5'), and R67743 (yi28d02.r1 *Homo sapiens* cDNA clone 140547 5'). Based upon sequence similarity, dx279_1 proteins and each similar protein or peptide may share at least some activity. The TopPredII computer program predicts a potential transmembrane domain within the dx279_1 protein sequence centered around amino acid 70 of SEQ ID NO:18.

Clone "gm243_1"

A polynucleotide of the present invention has been identified as clone "gm243_1". gm243_1 was isolated from a human adult uterus cDNA library using methods which are selective for cDNAs encoding secreted proteins (see U.S. Pat. No. 5,536,637), or was identified as encoding a secreted or transmembrane protein on the basis of computer analysis of the amino acid sequence of the encoded protein. gm243_1 is a full-length clone, including the entire coding sequence of a secreted protein (also referred to herein as "gm243_1 protein").

The nucleotide sequence of gm243_1 as presently determined is reported in SEQ ID NO:19. What applicants presently believe to be the proper reading frame and the predicted amino acid sequence of the gm243_1 protein corresponding to the foregoing nucleotide sequence is reported in SEQ ID NO:20.

The EcoRI/NotI restriction fragment obtainable from the deposit containing clone gm243_1 should be approximately 3500 bp.

The nucleotide sequence disclosed herein for gm243_1 was searched against the GenBank and GeneSeq nucleotide sequence databases using BLASTN/BLASTX and FASTA search protocols. gm243_1 demonstrated at least some similarity with sequences identified as H39507 (yo54c09.r1 *Homo sapiens* cDNA clone 181744 5'). Based upon sequence similarity, gm243_1 proteins and each similar protein or peptide may share at least some activity.

Deposit of Clones

Clones bd379_1, bp121_2, bp646_10, cf50_1, cw1543_3, da389_1, dd71_2, dm221_1, dx279_1 and gm243_1 were deposited on Mar. 13, 1997 with the American Type Culture Collection (10801 University Boulevard, Manassas, Va. 20110-2209 U.S.A.) as an original deposit under the Budapest Treaty and were given the accession number ATCC 98361, from which each clone comprising a particular polynucleotide is obtainable. All restrictions on the availability to the public of the deposited material will be irrevocably removed upon the granting of the patent, except for the requirements specified in 37 C.F.R. §1.808(b).

Figure 1B:
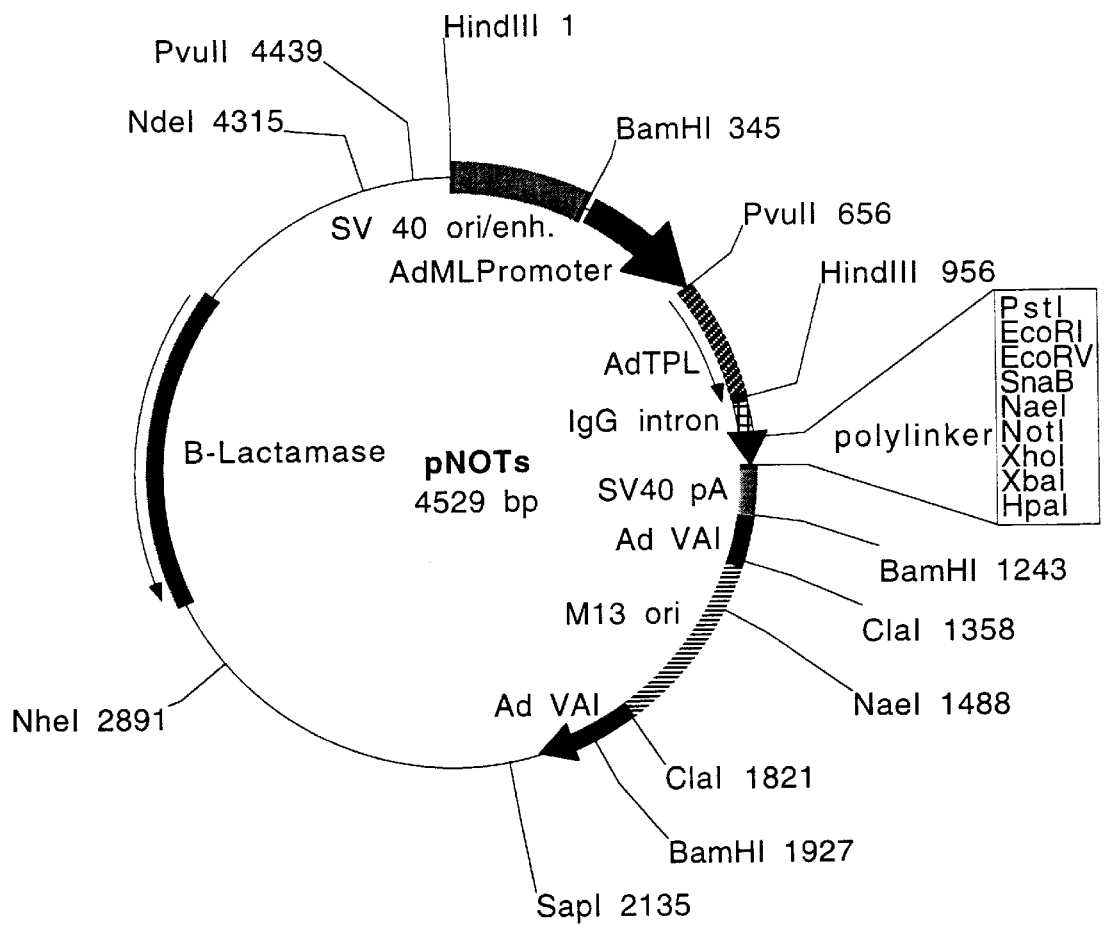

Each clone has been transfected into separate bacterial cells (*E. coli*) in this composite deposit. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIG. 1. The pED6dpc2 vector ("pED6") was derived from pED6dpc1 by insertion of a new polylinker to facilitate cDNA cloning (Kaufman et al., 1991, *Nucleic Acids Res.* 19: 4485–4490); the pNOTs vector was derived from pMT2 (Kaufman et al., 1989, *Mol. Cell. Biol.* 9: 946–958) by deletion of the DHFR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of the oligonucleotide probe that was used to isolate each full-length clone is identified below, and should be most reliable in isolating the clone of interest.

| Clone | Probe Sequence |
| --- | --- |
| bd379_1 | SEQ ID NO:21 |
| bp121_2 | SEQ ID NO:22 |
| bp646_10 | SEQ ID NO 23 |
| cf50_1 | SEQ ID NO 24 |
| cw1543_3 | SEQ ID NO:25 |
| da389_1 | SEQ ID NO:26 |
| dd71_2 | SEQ ID NO:27 |
| dm221_1 | SEQ ID NO:28 |
| dx279_1 | SEQ ID NO:29 |
| gm243_1 | SEQ ID NO:30 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-phosphoramadite) (Glen Research, cat. no. 10- 1953)).

The design of the oligonucleotide probe should preferably follow these parameters:

(a) It should be designed to an area of the sequence which has the fewest ambiguous bases ("N's"), if any;
(b) It should be designed to have a $T_m$ of approx. 80° C. (assuming 2° for each A or T and 4 degrees for each G or C).

The oligonucleotide should preferably be labeled with g-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6× SSC (20× stock is 175.3 g NaCl/liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2× SSC/0.5% SDS at room temperature without agitation, preferably followed by 500 mL of 2× SSC/0.1% SDS at room temperature with gentle shaking for 15 minutes. A third wash with 0.1× SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10 773–778 (1992) and in R. S. McDowell, et al., J. Amer. Chem. Soc. 14 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form of such protein may be obtained by expression of the disclosed full-length polynucleotide (preferably those deposited with ATCC) in a suitable mammalian cell or other host cell. The sequence of the mature form of the protein may also be determinable from the amino acid sequence of the full-length form.

The present invention also provides genes corresponding to the cDNA sequences disclosed herein. "Corresponding genes" are the regions of the genome that are transcribed to produce the mRNAs from which the cDNA sequences are derived and any contiguous regions of the genome necessary for the regulated expression of such genes, including but not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Proteins and protein fragments of the present invention include proteins with amino acid sequence lengths that are at least 25% (more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

Species homologs of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide, as determined by those of skill in the art. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous, or related to that encoded by the polynucleotides.

The invention also includes polynucleotides with sequences complementary to those of the polynucleotides disclosed herein.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1 × SSC -or- 42° C.; 1 × SSC, 50% formamide | 65° C.; 0.3 × SSC |
| B | DNA:DNA | <50 | $T_B^*$; 1 × SSC | $T_B^*$; 1 × SSC |
| C | DNA:RNA | ≥50 | 67° C.; 1 × SSC -or- 45° C.; 1 × SSC, 50% formamide | 67° C.; 0.3 × SSC |
| D | DNA:RNA | <50 | $T_D^*$; 1 × SSC | $T_D^*$; 1 × SSC |
| E | RNA:RNA | ≥50 | 70° C.; 1 × SSC -or- 50° C.; 1 × SSC, 50% formamide | 70° C.; 0.3 × SSC |
| F | RNA:RNA | <50 | $T_F^*$; 1 × SSC | $T_F^*$; 1 × SSC |
| G | DNA:DNA | ≥50 | 65° C.; 4 × SSC -or- 42° C.; 4 × SSC, 50% formamide | 65° C.; 1 × SSC |
| H | DNA:DNA | <50 | $T_H^*$; 4 × SSC | $T_H^*$; 4 × SSC |
| I | DNA:RNA | ≥50 | 67° C.; 4 × SSC -or- 45° C.; 4 × SSC, 50% formamide | 67° C.; 1 × SSC |
| J | DNA:RNA | <50 | $T_J^*$; 4 × SSC | $T_J^*$; 4 × SSC |
| K | RNA:RNA | ≥50 | 70° C.; 4 × SSC -or- 50° C.; 4 × SSC, 50% formamide | 67° C.; 1 × SSC |
| L | RNA:RNA | <50 | $T_L^*$; 2 × SSC | $T_L^*$; 2 × SSC |
| M | DNA:DNA | ≥50 | 50° C.; 4 × SSC -or- 40° C.; 6 × SSC, 50% formamide | 50° C.; 2 × SSC |
| N | DNA:DNA | <50 | $T_N^*$; 6 × SSC | $T_N^*$; 6 × SSC |
| O | DNA:RNA | ≥50 | 55° C.; 4 × SSC -or- 42° C.; 6 × SSC, 50% formamide | 55° C.; 2 × SSC |
| P | DNA:RNA | <50 | $T_P^*$; 6 × SSC | $T_P^*$; 6 × SSC |
| Q | RNA:RNA | ≥50 | 60° C.; 4 × SSC -or- 45° C.; 6 × SSC, 50% formamide | 60° C.; 2 × SSC |
| R | RNA:RNA | <50 | $T_R^*$; 4 × SSC | $T_R^*$; 4 × SSC |

‡: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

†: SSPE (1 × SSPE is 0.15M NaCl, 10 mM $NaH_2PO_4$, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete.

*$T_B$ – $T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) – (600/N), where N is the number of bases in the hybrid, and [$Na^+$] is the concentration of sodium ions in the hybridization buffer ([$Na^+$] for 1 × SSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and InVitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human Interferon γ, Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6-Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11-Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9-Ciarletta, A., Giannotti, J., Clark, S. C. and Turner, K. J. In *Current Protocols in Immunology.* J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. U.S.A. 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci. U.S.A., 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class II $\alpha$ chain protein and an MHC class II $\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology*. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. U.S.A. 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. U.S.A. 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc.., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. W095/16035 (bone, cartilage, tendon); International Patent Publication No. W095/05846 (nerve, neuronal); International Patent Publication No. W091/07491 (skin, endothelium).

Assays for wound healing activity include, without limitation, those described in: Winter, *Epidermal Wound Healing* pps. 71–112 (Maibach, HI and Rovee, DT, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. U.S.A. 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744–1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419,1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W.Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. U.S.A. 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63: 1033–1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoiefic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Administration and Dosing

A protein of the present invention (from whatever source derived, including without limitation from recombinant and non-recombinant sources) may be used in a pharmaceutical composition when combined with a pharmaceutically acceptable carrier. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or antithrombotic factors, or sequentially. If administered sequentially, the attending physician will decide on the appropriate sequence of administering protein of the present invention in combination with cytokine(s), lymphokine(s), other hematopoietic factor(s), thrombolytic or antithrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 ng to about 10 mg, more preferably about 0.1 $\mu$g to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide selected from the group consisting of:

(a) a polynucleotide comprising the nucleotide sequence of SEQ ID NO:3;

(b) a polynucleotide comprising the nucleotide sequence of SEQ ID NO:3 from nucleotide 55 to nucleotide 1008;

(c) a polynucleotide comprising the nucleotide sequence of SEQ ID NO:3 from nucleotide 403 to nucleotide 981;

(d) a polynucleotide comprising the nucleotide sequence of the full-length protein coding sequence of clone bp121_2 deposited under accession number ATCC 98361;

(e) a polynucleotide encoding the full-length protein encoded by the cDNA insert of clone bp121_2 deposited under accession number ATCC 98361;

(f) a polynucleotide encoding a protein comprising the amino acid sequence of SEQ ID NO:4;

(g) a polynucleotide encoding a protein comprising a fragment of the amino acid sequence of SEQ ID NO:4, the fragment comprising the amino acid sequence of SEQ ID NO:4 from amino acid 119 to amino acid 309; and (h) a polynucleotide that hybridizes in 6× SSC at 65 degrees C. to any one of the polynucleotides specified in (a)–(g), and that has a length that is at least 25% of the length of SEQ ID NO:3.

2. The polynucleotide of claim 1 wherein said polynucleotide is operably linked to at least one expression control sequence.

3. A host cell transformed with the polynucleotide of claim 2.

4. The host cell of claim 3, wherein said cell is a mammalian cell.

5. A process for producing a protein encoded by the polynucleotide of claim 2, which process comprises:

(a) growing a culture of the host cell of claim 3 in a suitable culture medium; and (b) purifying said protein from the culture.

6. An isolated polynucleotide encoding a protein, wherein the protein is produced according to the process of claim 5.

7. The polynucleotide of claim 6, wherein the polynucleotide comprises the cDNA insert of clone bp121_2 deposited under accession number ATCC 98361.

8. The polynucleotide of claim 1, wherein the polynucleotide comprises the nucleotide sequence of SEQ ID NO:3.

9. The polynucleotide of claim 1, wherein the polynucleotide comprises the nucleotide sequence of SEQ ID NO:3 from nucleotide 55 to nucleotide 1008.

10. The polynucleotide of claim 1, wherein the polynucleotide comprises the nucleotide sequence of SEQ ID NO:3 from nucleotide 403 to nucleotide 981.

11. The polynucleotide of claim 1, wherein the polynucleotide comprises the nucleotide sequence of the full-length protein coding sequence of clone bp121_2 deposited under accession number ATCC 98361.

12. The polynucleotide of claim 1, wherein the polynucleotide encodes the full-length protein encoded by the cDNA insert of clone bp121_2 deposited under accession number ATCC 98361.

13. The polynucleotide of claim 1, wherein the polynucleotide encodes a protein comprising the amino acid sequence of SEQ ID NO:4.

14. The polynucleotide of claim 1, wherein the polynucleotide encodes a protein comprising a fragment of the amino acid sequence of SEQ ID NO:4, the fragment comprising the amino acid sequence of SEQ ID NO:4 from amino acid 119 to amino acid 309.

* * * * *